(12) United States Patent
Meka et al.

(10) Patent No.: US 8,002,712 B2
(45) Date of Patent: Aug. 23, 2011

(54) BREATH AND BREATH CONDENSATE ANALYSIS SYSTEM AND ASSOCIATED METHODS

(76) Inventors: Vikas V. Meka, Gainesville, FL (US); Neil R. Euliano, Gainesville, FL (US); Craig T. Flanagan, Bakersfield, CA (US); Brent Joseph Lutz, Lakewood, CO (US)

( * ) Notice: Subject to any disclaimer, the term of this patent is extended or adjusted under 35 U.S.C. 154(b) by 957 days.

(21) Appl. No.: 11/627,508

(22) Filed: Jan. 26, 2007

(65) Prior Publication Data

US 2007/0173731 A1     Jul. 26, 2007

Related U.S. Application Data

(60) Provisional application No. 60/762,303, filed on Jan. 26, 2006.

(51) Int. Cl.
*A61B 5/08* (2006.01)
(52) U.S. Cl. .......... 600/543; 600/538; 600/529
(58) Field of Classification Search .......... 600/538–543, 600/529, 532; 73/23.3
See application file for complete search history.

(56) References Cited

U.S. PATENT DOCUMENTS

| | | | |
|---|---|---|---|
| 4,202,352 A * | 5/1980 | Osborn | 600/532 |
| 4,558,708 A * | 12/1985 | Labuda et al. | 600/532 |
| 4,607,501 A | 8/1986 | Vanlier | |
| 4,670,026 A * | 6/1987 | Hoenig | 95/73 |
| 5,042,501 A * | 8/1991 | Kenny et al. | 600/532 |
| 5,284,054 A * | 2/1994 | Loebach | 73/23.3 |
| 6,582,376 B2 * | 6/2003 | Baghdassarian | 600/543 |
| 6,585,661 B1 | 7/2003 | Hunt et al. | |
| 6,679,250 B2 * | 1/2004 | Walker et al. | 128/200.21 |
| 6,723,056 B1 * | 4/2004 | Alving et al. | 600/543 |
| 7,118,537 B2 | 10/2006 | Baddour | |
| 7,144,741 B2 | 12/2006 | Rothe et al. | |
| 2004/0024330 A1 | 2/2004 | Djupesland et al. | |
| 2004/0127808 A1 | 7/2004 | Vaughan et al. | |
| 2004/0138577 A1 * | 7/2004 | Kline | 600/543 |
| 2004/0162500 A1 | 8/2004 | Kline | |
| 2004/0220498 A1 | 11/2004 | Li et al. | |
| 2004/0236244 A1 | 11/2004 | Allen et al. | |
| 2005/0137491 A1 | 6/2005 | Paz et al. | |
| 2005/0208614 A1 | 9/2005 | Kline et al. | |
| 2006/0133960 A1 | 6/2006 | Ahmad | |
| 2006/0279167 A1 | 12/2006 | Turner | |
| 2007/0056588 A1 * | 3/2007 | Hayek | 128/205.25 |
| 2009/0137920 A1 * | 5/2009 | Colman et al. | 600/543 |

FOREIGN PATENT DOCUMENTS

DE          20001995          8/2000

\* cited by examiner

*Primary Examiner* — Patricia C Mallari
*Assistant Examiner* — Michael D'Angelo
(74) *Attorney, Agent, or Firm* — Allen, Dyer, Doppelt, Milbrath & Gilchrist, P.A.

(57) ABSTRACT

A system for collecting an exhaled breath sample and exhaled breath aerosol from a subject includes a condensation chamber having an outerwall defining an interior space. The outer wall has an inlet port and an outlet port therethrough in fluid communication with the interior space. The inlet port is placeable in fluid communication with an exhaled breath sample of the subject. A condensation element is positioned within the condensation chamber interior space and has a shape tapering downwardly toward a bottom tip thereof. A condensation of fluid on the condensation element is enhanced through various elements. A collection area is positioned within the condensation chamber's interior space beneath the condensation element bottom tip. The collection area is for collecting condensate accumulating on an outer surface of the condensation element and dropping from the tip thereof.

30 Claims, 14 Drawing Sheets

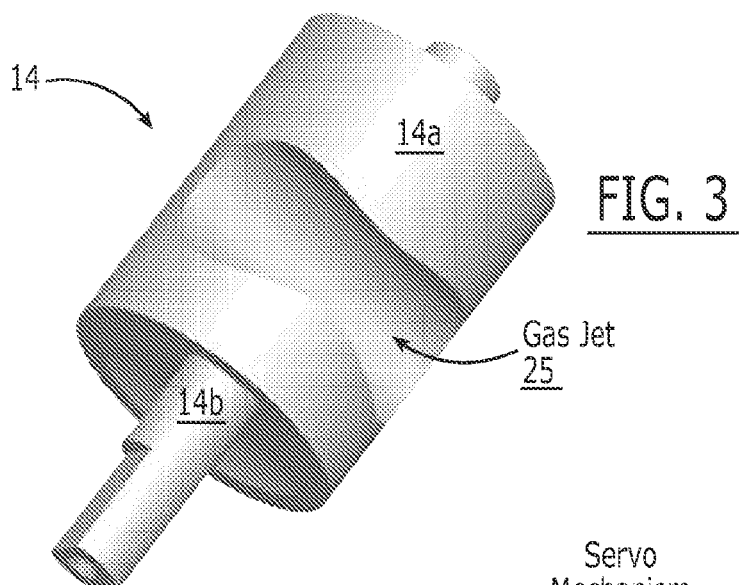
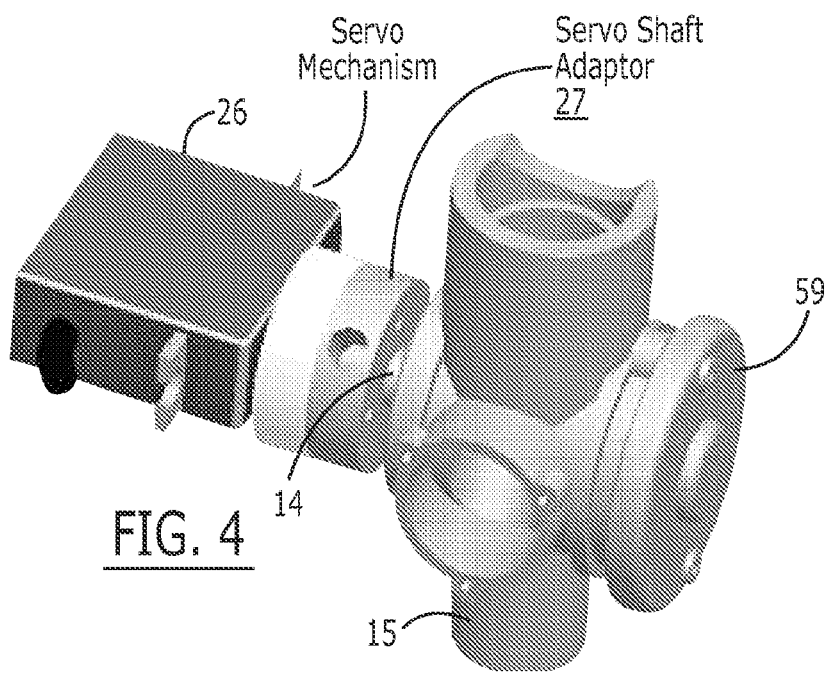
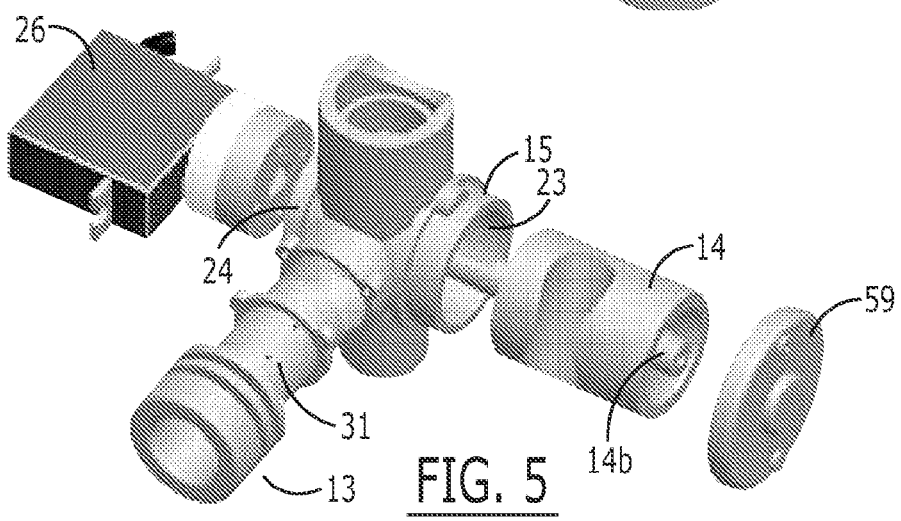

BREATH AND BREATH CONDENSATE ANALYSIS SYSTEM AND ASSOCIATED METHODS

CROSS-REFERENCE TO RELATED APPLICATION

This application claims priority to provisional application Ser. No. 60/762,303, filed Jan. 26, 2007, entitled "Breath and Breath Condensate Analysis System and Associated Methods."

BACKGROUND OF THE INVENTION

1. Field of the Invention

The present invention relates to systems and methods for analyzing breath samples, and, more particularly, to such systems and methods for analyzing samples of breath condensate.

2. Description of Related Art

It is known in the art to analyze exhaled breath samples, for example, as a means to determine blood alcohol levels, and in anesthesia and critical care where inhalation anesthetic agents and exhaled carbon dioxide are routinely monitored. Infectious or metabolic diseases liberate specific odors that are characteristic of disease presence. Chromatographic techniques have identified volatile compounds in exhaled breath that can serve as potential markers for specific diseases. For example, *Helicobacter pylori* can be detected by a breath test for ammonia or radio-labeled carbon dioxide, and diabetic ketosis can produce acetone, which can be detected in the breath.

It is believed that exhaled breath sensing can provide noninvasive, point-of-care solutions to many medical applications, including illicit drug detection and medical condition diagnosis. In theory, any volatile compound in the blood stream can be found in the breath. Diagnostic breath test methods are known, but are expensive and time consuming, and must be performed in a laboratory by a trained technician.

Breath condensate analysis is a special case of breath analysis in which exhaled gas samples are cooled to a point at which the humidity in such samples condenses into a liquid, which is in turn collected. It is assumed that volatile markers, as well as biomolecules traveling as aerosols, partition into the condensate as well, and can be detected upon analysis of the condensate. It is known that a large variety of biomarkers can be found, including hydrogen peroxide, ammonia, and various peptides. As with normal breath gas analysis, such analytical methods are time consuming and require a trained technician and laboratory.

Condensate collection typically requires 10-15 minutes of breathing in order to obtain a 1-2 mL sample. This sample is then collected by syringe and transported to an analysis device (e.g., gas chromatograph/mass spectrometer, GC-MS). For example, Jaeger (a subsidiary of VIASYS Healthcare) produces a breath condensate collector called the ECoScreen, which uses gravity to collect condensate at the bottom of a macro-scale cooling tube. It is reproducible and prevents contamination by saliva, but, as mentioned above, requires 10-15 minute breathing times, as well as manual sample removal/transport. This causes discomfort for the patient, and requires a trained technician to handle and process the breath condensate samples.

Known existing exhaled breath condensate (EBC) collectors remain cumbersome and expensive, and utilize an external cooling system (often very bulky and power hungry) to condense out the breath. After collection of breath condensate the sample must be manually extracted and injected into sampling vials for appropriate analysis, thus exposing the sample to potential contamination and handling errors. The lack of a standardized method for how breath condensate is collected and handled makes it rather complicated for researchers to readily compare results and draw conclusions.

Recently, the American Thoracic Society (ATS) and European Respiratory Society (ETS) have jointly released guidelines for the collection and measurement of EBC biomarkers. The steps recommended by the task force are comprehensive and an excellent start for standardization of EBC collection. However, the main emphasis of the guidelines is to instruct researchers on the different variables that should be reported in literature, and comparing results and drawing conclusions from data measured with different environmental conditions still remains a challenge that has not been addressed.

Having an EBC collection device that is inexpensive, portable, and self-contained on the market would offer users an incentive to purchase and avoid custom development. It is difficult to make progress in EBC analysis if the condensate concentrations differ in back-to-back assays by as much as 50% due to poor collection techniques. Furthermore, a majority of known EBC devices collect the entire exhaled breath to maximize the total volume of condensate. It is well known that individuals have varying degrees of respiratory dead space and collecting the entire breath causes significant variability in measured results. Having a standardized collection system would help minimize variability between assays.

To date, there does not appear to be a strong push to utilize microfluidics for breath condensate analysis, which may be owing to lack of a direct interface between the macro sampling tools to the micro analytical procedures. None of the known EBC collection units addresses a means for efficient handling and transfer of condensate to an analytical system, leaving researchers to extract and prepare samples manually. Additionally, since analysis is done with macro-scale spectroscopy instruments such as gas and liquid chromatography, large sample volumes are required. Collection of EBC requires controlled breathing and as such it is desirable to collect for a short duration of time. Prolonged collection times can result in subjects hyperventilating and introducing uncertainties in collected sample. By utilizing microfluid-based sensors that could potentially be directly integrated into the EBC collection device, the need to sample for a long time can be removed and allow collection of samples with finer time resolution.

Therefore, it would be desirable to provide a system and method that can decrease the requisite collection time, thus alleviating patient involvement, and can automate the collection and analysis of breath condensate, such that reliable, point-of-care diagnostic information could be obtained. It would be especially desirable to provide such a system and method that can be used in the absence of an external cooling system.

SUMMARY OF THE INVENTION

The present invention is directed to an instrument for measuring breath and breath condensate analysis. In a particular embodiment, the instrument comprises a first, preferably disposable, element that includes an inlet for receiving expired breath and a condensate trap for holding and condensing the received expired breath containing volatiles, aerosols, and other bio-markers of interest. A valve operates between a sampling orientation for placing the trap in fluid communication with the inlet and a non-sampling orientation for closing the trap off from the inlet. Means are provided for moving the valve between the first and the second orientations.

A condensing element is positioned within the trap for accelerating the formation of a condensation droplet. A collection element is positioned to receive a formed droplet, the collection element in fluid communication with an analysis device positionable within the disposable element.

The disposable element is configured for mating with a second, preferably non-disposable element containing electronics and control devices for operating the valve and receiving data from the analysis device.

The present invention provides a technology that accelerates and simplifies breath condensate analysis in order to allow for inexpensive, high-volume studies and/or practical in-home or clinical use.

In a particular embodiment, an EBC collection system, which also collects aerosols and will be referred to hereafter as an exhaled breath aerosol and condensation system (EBAC) is provided that is simple to use, sufficiently lightweight for a handheld implementation, inexpensive for widespread use, and independent of external cooling systems. A system is further provided that uses microfluid techniques in breath condensate analysis that can greatly improve collection technology and enable more rapid and commercial progress in this area.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 3 is a side perspective view of the spindle.

FIG. 4 is a side perspective view of the spindle, valve, and cap assembly with a servo/servo shaft adapter attached thereto.

FIG. 5 is a side perspective exploded view of the assembly.

DETAILED DESCRIPTION OF THE PREFERRED EMBODIMENTS

Figure 1A:
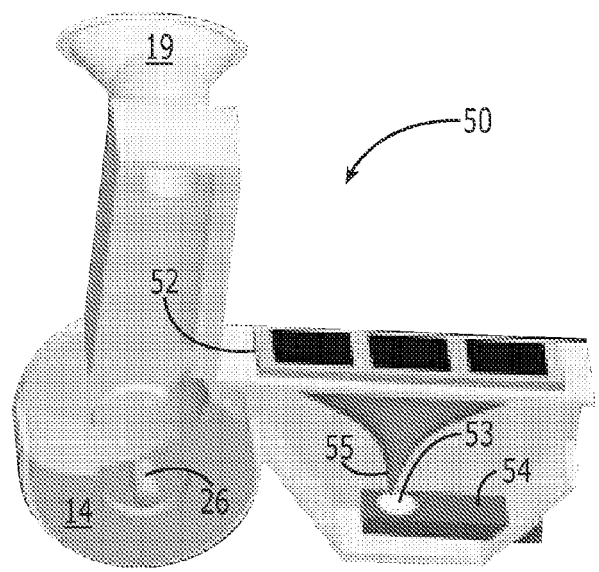
FIGS. 1A and 1B are cutaway side perspective views of the condensate trap in position for receiving inspired or fresh gas (FIG. 1A) and for channeling the received gas to the analytical device (FIG. 1B).

A description of the preferred embodiments of the present invention will now be presented with reference to FIGS. 1A-22.

In a preferred embodiment of the invention, a system 10 for analyzing breath, breath aerosols, and breath condensate comprises a collection and analysis device 50 that is preferably disposable and is usable with a complementary electrical instrument housing 51, which may be non-disposable. The system 10 achieves automated extraction of condensate fluid from exhaled deep lung gas and immediate analysis by a miniaturized sensing system, such as that which may be implemented on a microfluidic device. The system 10 includes features for improved gas flow, condensate fluid extraction, and communication of the collected condensed fluid extract to the analysis system.

In the preferred embodiment of the invention, the automated provision of a drop of exhaled breath condensate to a miniaturized analysis device is accomplished by means of a Peltier cooler-based exhalation condensate trap. The condensation trap comprises structures and mechanisms implemented as an integrated, preferably single-use, disposable package 50.

Exhaled gas (ideally end-tidal, alveolar, or deep lung gas) is directed from a mouthpiece 19 through a closed pathway containing a condensation element 52 designed to attract and condense vapor-phase humidity, including aerosols, from the exhaled gas stream. Condensate accumulates on the condensing element 52 and is gravimetrically driven to the tip 55 of this uniquely shaped element upon which a large droplet eventually forms. When the droplet reaches sufficient size, it falls into a concave collection chamber 53 located on a miniaturized analysis chip 54. The chip 54, which may contain microfluidic handling capability, then processes the fluid such that constituent chemical, biochemical, and biological species can be identified and/or quantified.

Gas flow through the device 50, in a preferred embodiment, is controlled by means of a rotary three-way valve mechanism consisting of a uniquely shaped spindle 14 housed in a three-outlet arrangement. The spindle mechanism 14 is rotated to one of two discrete positions by means of an external actuator 26 in response to airway gas flow and/or airway gas concentrations. Gas diversion reciprocates between states of fluid communication of the airway with inspired or fresh gas (FIGS. 1A and 1C) and fluid communication of the airway with the condensation pathway (FIGS. 1B and 1D).

Gas diversion can be accomplished with an electro-mechanical sensor-based scheme. With respect to the sensor elements, the invention makes use of at least one of carbon dioxide partial pressure and exhalation flow/volume. These are measured using sensor systems disposed in fluid communication with the breathing gas. These systems comprise carbon dioxide and flow sensing systems. The flow sensor can comprise, for example, a differential pressure flow element, although this is not intended as a limitation, and those skilled in the art will recognize that the substitution of alternative flow measurement technologies such as hot-wire anemometry, vortex shedding, ultrasonic time-of-flight, etc., could also be used.

Figure 1B:
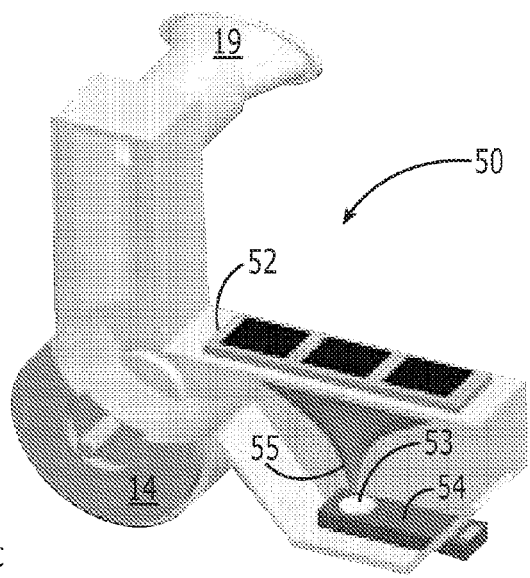

The flow sensor employed in a preferred embodiment can comprise a fixed-orifice flow restriction element located proximal to the spindle mechanism 14 and distal of the mouthpiece 19, with pressure taps on either side (visible as small holes in the flow sensor in FIGS. 1A and 1B). The differential pressure developed across the fixed orifice in such a configuration is a mathematical function of airway flow. This differential pressure is measured by a differential pressure transducer, which, in turn, sends its output to a differential input instrumentation amplifier located in the non-disposable portion 51 of the system 10. Such fixed-orifice flow sensors lend themselves to simple fabrication, produce little or no hysteresis, and have output flow signals somewhat resistant to the distorting effects of sputum and condensate accumulation in the sensor. A drawback of such flow sensing technology is the inherent nonlinearity of the flow versus differential pressure signal, requiring high-gain pressure amplification in the low-flow regime of operation.

Figure 7:
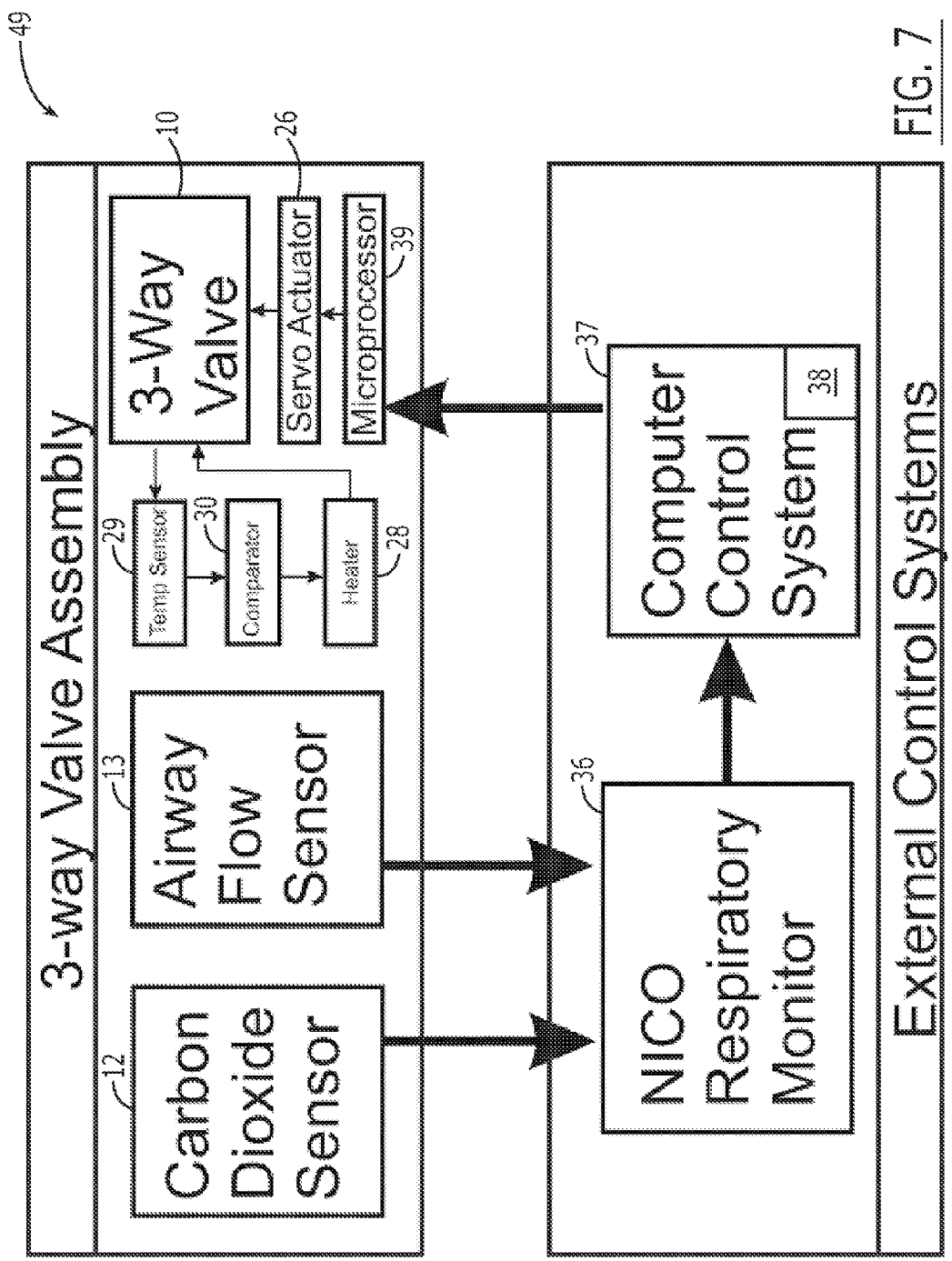
FIG. 7 is a flowchart of the breath capture system.

The invention comprises a breath capture valve 49 (FIGS. 1C and 1D) used in an electro-mechanical sensor-based scheme 11 (FIG. 7). The sensor elements, primarily used for triggering state changes, can comprise, for example, devices that measure one or more of carbon dioxide partial pressure 12 and exhalation flow/volume 13. Additional types of sensors that may detect or correlate with the difference between alveolar and dead-space gas may be used in the invention. These sensors can include sensors responsive to oxygen, hydrogen, various volatile organic compounds (VOCs) found in the exhaled breath, etc. The sensors 12,13 are disposed in fluid communication with the breathing gas. Carbon dioxide partial pressure 12 is measured in a preferred embodiment using non-dispersive infrared (NDIR) spectroscopy technology, while flow/volume 13 is measured using a differential pressure flow element, although alternate technologies can be substituted and are not intended to be limiting. For example, the carbon dioxide sensor 12 in the exemplary embodiment can be replaced with a real-time oxygen sensor as real-time oxygen traces morphologically mimic the inverse of carbon dioxide traces.

Figure 1C:
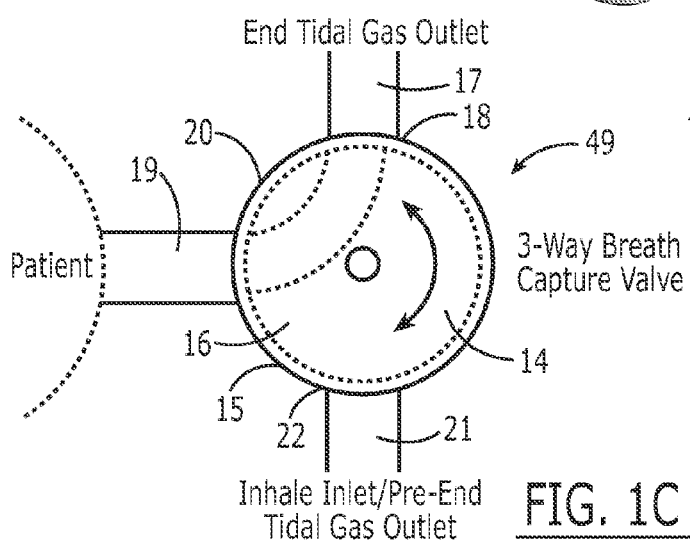
FIGS. 1C and 1D illustrate two positions of the three-way breath capture valve, with FIG. 1C sampling the end tidal gas and FIG. 1D transmitting the inhalation gas and the exhalation dead space outside the system.
Figure 1D:
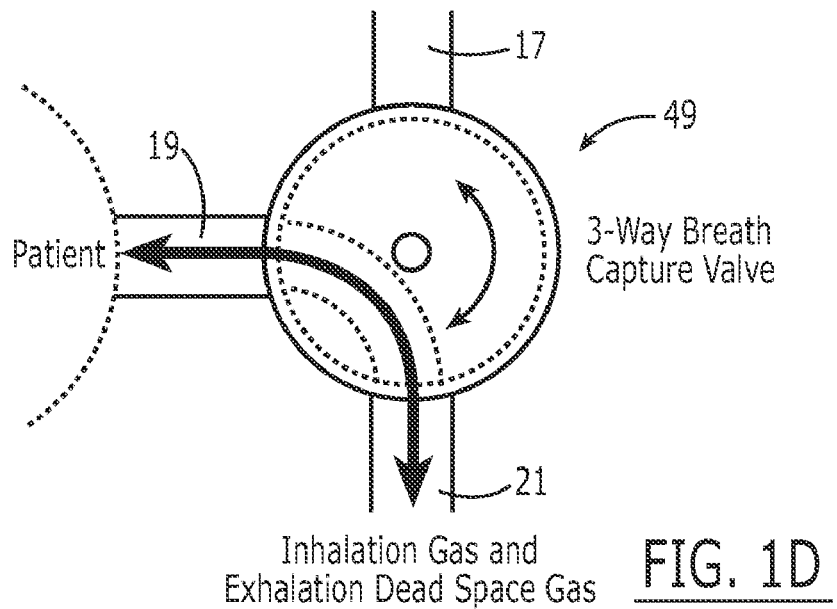
Figure 2:
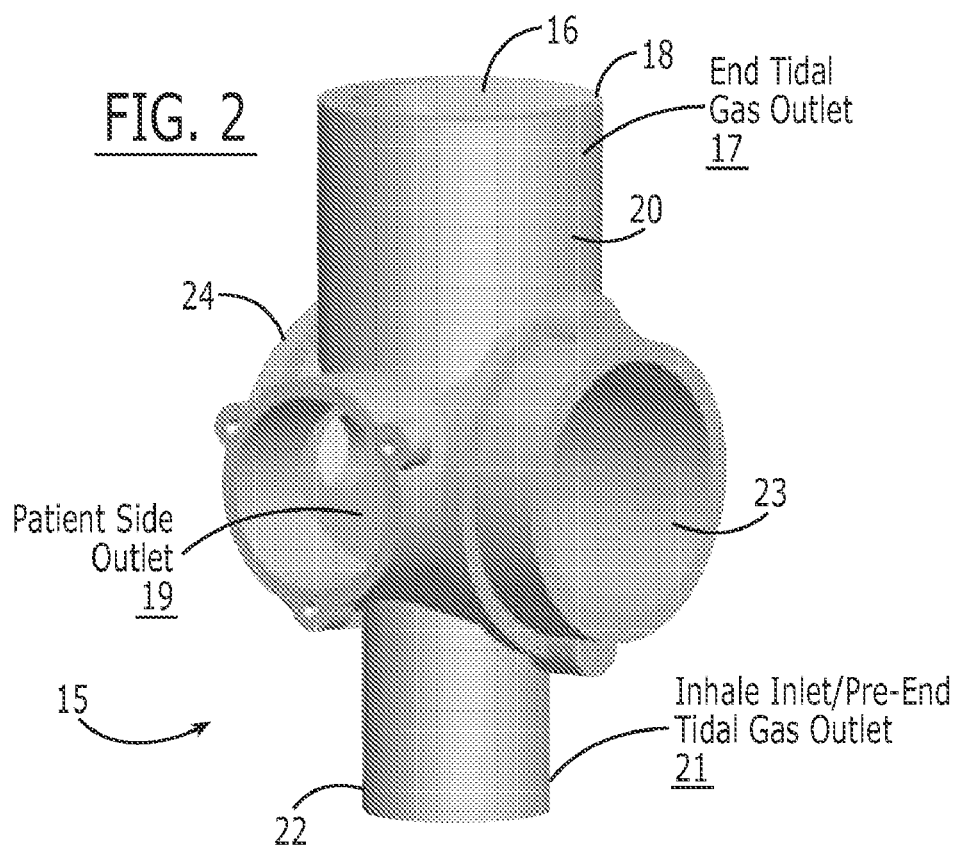
FIG. 2 is a side perspective view of the valve cylinder.
Figure 6A:
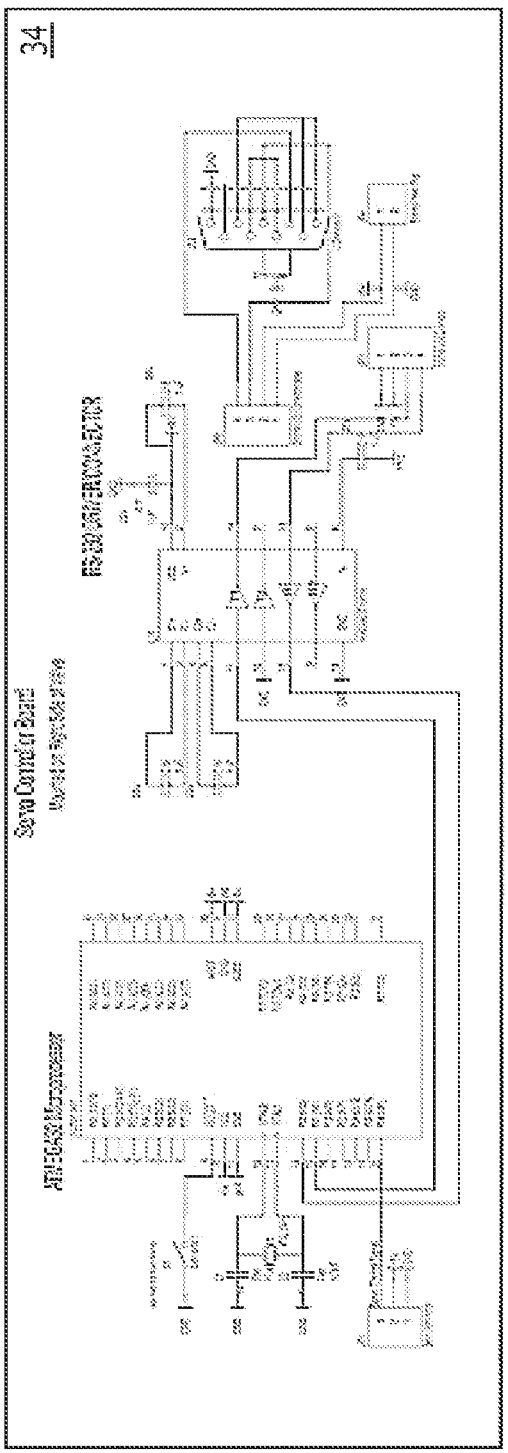
FIGS. 6A and 6B are exemplary circuit schematics of the breath capture apparatus, with FIG. 6A directed to a servo controller board and FIG. 6B, to a temperature controller board.
Figure 6B:
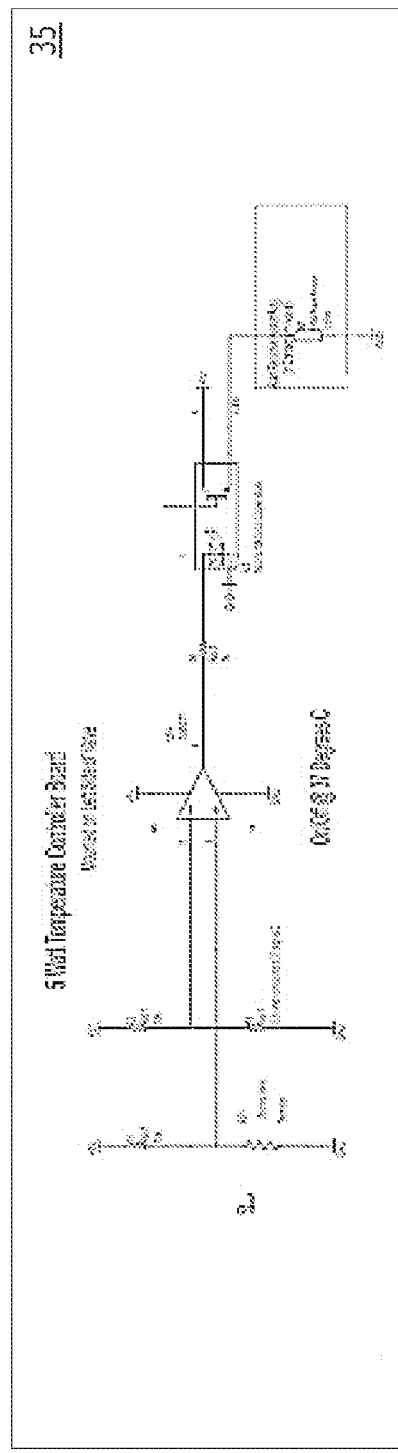

The mechanical elements of the valve 49 comprise a cylinder/spindle system that serves as a flow-diverting three-way valve. In an alternate embodiment to be discussed in the following, a four-way valve can be used. Flow diversion is accomplished by axial rotation of the spindle 14 inside the cylinder 15 (FIGS. 1C-2). The cylinder 15 has a plurality of ports into a lumen 16 thereof, including an end tidal gas outlet 17 at a first end 18 thereof, a patient side outlet 19 into a side wall 20 thereof, and an inhale inlet/pre-end tidal gas outlet 21 at a second end 22 opposed to the first end 18 thereof. Two additional ports 23,24 are provided for admitting the spindle 14 into the lumen 16 (see FIG. 10).

The spindle 14 (FIG. 3) comprises a machined "jet," or depression, 25 that ensures fluid communication of two of the three flow outlets when the valve 49 is in either of two states, as well as ensuring smooth or uninterrupted gas flow during valve state transition. Rotation of the spindle 14 is effected, in a preferred embodiment, though the use of a mechanical servo actuator 26 (FIG. 4) connected to the spindle 14 with a coupling mechanism such as a servo shaft adaptor 27. The servo actuator 26 can use the pulse width of an incoming pulse-width-modulated (PWM) pulse train to impart angular actuation. Those skilled in the art would recognize that other rotary actuators may be selected, and that this embodiment is not intended to be limiting.

In order to prevent condensate formation on the gas-contacting surfaces of the three-way valve 49, a feedback-controlled heater 28 is used to heat the valve 49 to slightly above body temperature. This heater 28 can comprise, for example, a resistive heating element held in direct contact with the valve 49 or enclosure by means of adhesive or magnets, a thermistor element 29 mounted in direct contact with the valve 49 or enclosure by similar means, and an electronic comparator circuit 30 that ensures that power to the resistive heating element 28 is maintained when the temperature of the valve 49 is below the target value. This arrangement ensures that water vapor in the exhalation gas stream will not condense on the walls of the valve 49. Such condensate formation might trap or adhere to chemical species of interest in the exhalation gas stream, thus reducing the quantity of the species available in the end tidal gas for analysis In addition to heating, a special highly inert coating called Siltek (Restek Corp, State College, Pa.) is used on the valve 49 of the preferred embodiment to prevent adsorption and breakdown of analytes owing to interaction with the active surface chemistry of the valve 49. It should be noted that while such adsorption issues are generally not problematic for hydrocarbons; active compounds such as alcohols, amines, phenols, and drugs are typically susceptible. The Siltek process consists of heating the parts to 400° C., during which time the coating is deposited in a thin film on the surface of the parts. This surface coating is highly inert, effectively minimizing adsorption phenomena.

The spindle 14, in the preferred embodiment, can be rotated by a Hi-Tec (Poway, Calif.) HS-81 analog microservo 26. This servo 26 produces 90 degrees of angular rotation (sufficient to change a three-way valve state) in 90 msec. This switching speed is sufficient for the application at hand. Higher switching speeds might be attained by the use of other rotary actuators, as will be appreciated by those skilled in the art. The outer diameter of the spindle 14 and the inner diameter of the cylinder 15 are precisely bored/honed to ensure a relatively small radial clearance. This small clearance ensures that significant quantities of gas will not escape though the valve 49 to the closed flow pathway. Sealants, O-rings, and other devices to block flow or seal the pneumatic pathway are preferably not used in the invention for three reasons:

1. To ensure gas flow pathway chemical inertness by maintaining the homogeneity of materials in this flow pathway;

2. To ensure that the valve components can be easily cleaned (using an autoclave) and quickly reassembled; and 3. To minimize the torque required to rotate the spindle during valve state transition, thus reducing actuator size, weight, and power requirements.

The functional diameter of the gas flow path in the spindle 14 and sleeves of the cylinder 15 is 11 mm in a particular embodiment. This large diameter ensures that breathing gas has little resistance to flow, thus producing only mild proximal pressure (patient side) change in response to airway flow. This design achieves a minimization of patient discomfort during use. The spindle 14 is designed to ensure that a smooth transition between cylinder outlet ports occurs during spindle rotation. This is done, in like fashion, to prevent proximal pressure transients that might be noticeable and bothersome to the patient.

The system 11 can make use of two sensor technologies for making decisions on when to rotate the valve assembly 49, although, as discussed above, other sensor technologies may be used without loss of generality. These systems consist of carbon dioxide 12 and flow sensing 13 systems, as noted above. The flow sensor 13 may comprise, for example, a differential pressure flow element as are known in the art. Those skilled in the art will recognize that the substitution of alternative flow measurement technologies such as hot-wire anemometry, vortex shedding, ultrasonic time-of-flight, etc. can be made without departing from the spirit of the invention. The flow sensor 13 employed in the preferred embodiment comprises a fixed-orifice flow restriction with pressure taps on either side (visible as small holes 31 in the flow sensor 13 in FIG. 5). The differential pressure developed across the fixed orifice 31 is a mathematical function of airway flow. This differential pressure is measured by a differential pressure transducer which, in turn, sends its output to a differential input instrumentation amplifier, as discussed above. The amplifier, in this case, is located in the external NICO monitor. Such fixed-orifice flow sensors lend themselves to simple fabrication, produce little or no hysteresis, and have output flow signals somewhat resistant to the distorting effects of sputum and condensate accumulation in the sensor. In a preferred embodiment, a fixed-orifice flow transducer can be made out of metal and coated with the inert Siltek process. This embodiment minimizes the effects of analyte/surface chemistry interaction and condensate formation immediately distal to the patient airway 19.

The three (or four, in an alternate embodiment) outlets or sleeves on the cylinder of the invention are designed to be compatible with press-fit respiratory fittings, allowing the clinician greater flexibility in the choice of external fittings attached to the invention. Indeed, the top sleeve of the cylinder, through which the end tidal breathing gas flows, is compatible both on the inner and outer side of the sleeve, with respiratory press-fit fittings. A noticeable dimple in this outlet exists to allow non-interference fit of respiratory elbow fittings, press fit into the interior of the sleeve. It should be noted that any number of configurations compatible with external connectors or fitting might be employed.

A condensate trap may be attached to the outlet of the valve supplying end-tidal gas. Such a condensate trap can comprise a plastic tube with a duckbill or similar check valve located at its base attached directly to the outlet of the valve. The plastic tube can be surrounded by a heat-conductive metal sleeve cooled by some external means. Thus passing end tidal gas can be cooled inside this plastic/tube surrounded by the cooled metal sleeve and the vapor would condense and rainout in the tube for later collection and analysis. Other methods of collecting samples in solid, liquid, or gas phase known in the art can also be substituted. In addition, a small spit trap may be optionally integrated into the assembly distal to the mouth piece and proximal to the valve mechanism for trapping bulk saliva.

In its preferred embodiment, the invention contains on-board electronic circuitry 34,35. This electronic circuitry, shown in FIGS. 6A and 6B, includes an Atmel (San Jose, Calif.) ATMEGA32 RISC microcontroller with 32 k of flash memory. The embedded microcontroller code produces a variable frequency logic-level pulse-train to control the angular position of the attached servo mechanism, as well as RS-232 communications code, allowing the microcontroller to communicate with an external microcomputer. An exemplary configuration being used for RS-232 communications comprises 9600 baud, 8 bits, one stop bit, no parity. The interface chip being used for RS-232 communications can be the Maxim (Sunnyvale, Calif.) MAX232. In addition, a second circuit card 35 holds the temperature control comparator circuit for the feedback temperature control system. Power to the electronics can be supplied by an external DC power supply, for example.

FIG. 7 provides a global view of the control strategy used for the preferred embodiment of the invention. Here a NICO respiratory monitor 36 is used to collect data from on-board carbon dioxide 12 and flow 13 sensors, data from which are fed by way of an RS-232 link to an external microcomputer 37 running a dedicated software program 38. This dedicated software program 38 watches real-time carbon dioxide and flow/volume data and makes decisions on when to trigger rotation of the valve 49. Such decisions are preferably based on both carbon dioxide partial pressure during exhalation and exhalation flow and volume levels (see timing diagram of FIG. 8). The external microcomputer 37 then forwards its decision to rotate the valve 49 via an RS-232 link to the on-board ATMEL microcontroller 39. The ATMEL microcontroller then requests that the servo change position by altering the frequency of a logic pulse train sent to the servo 26. Those skilled in the art will recognize that the external NICO monitor and an external microcomputer are not intended as limitations on the invention.

FIGS. 2-5 and 9-12 show elements of the valve design as implemented in an exemplary embodiment. An exploded view of the valve system 49 is given in FIG. 5. Preferably the apparatus is sufficiently small to be housed in a handheld device. The valve cap 59 of FIG. 9 includes a first recess 59a for housing the cylinder wall 14a of the spindle 14, and a second, central recess 59b for housing the spindle shaft 14b.

Figure 8:
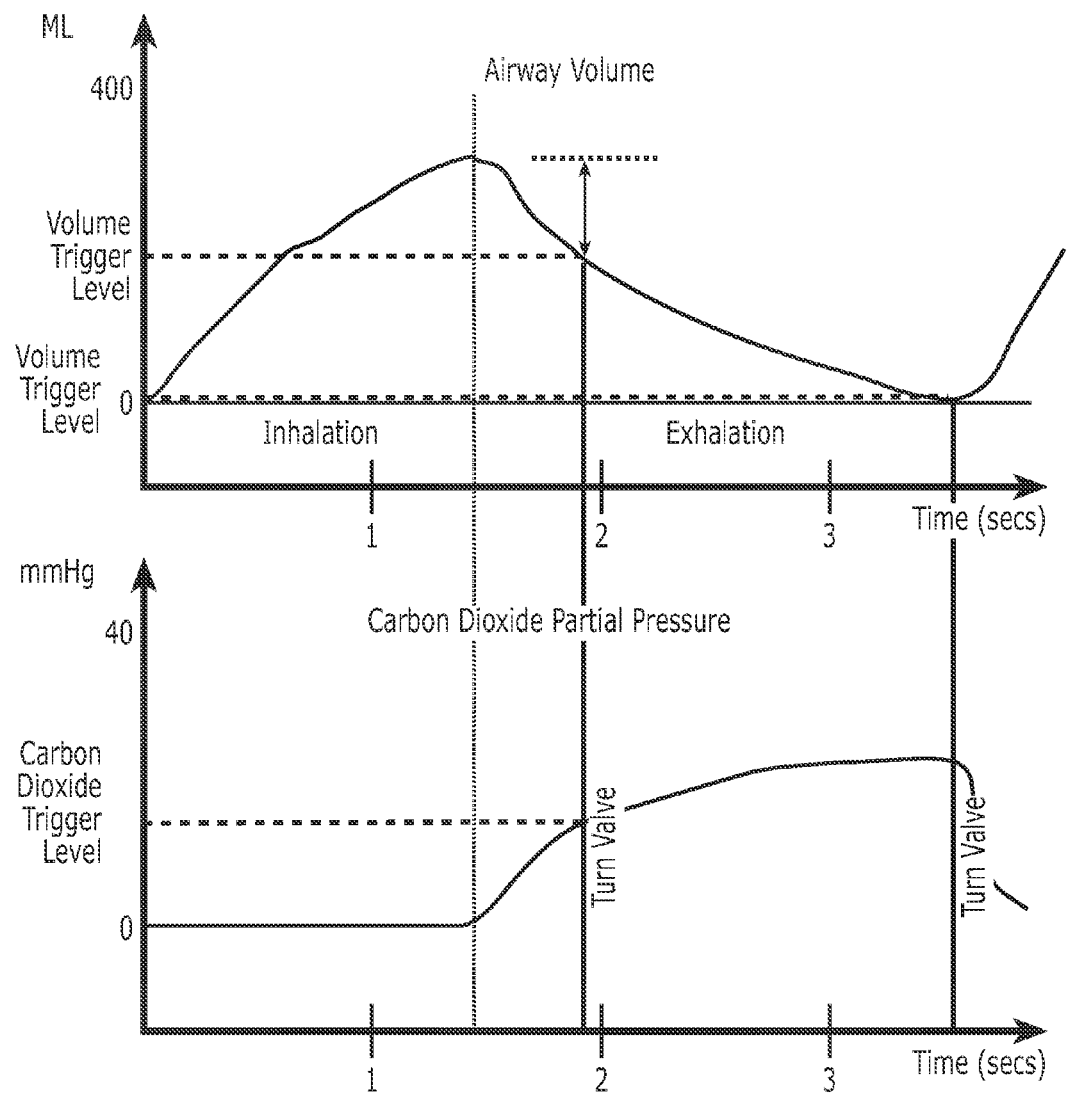
FIG. 8 is a timing diagram for triggering valve rotation.
Figure 9:
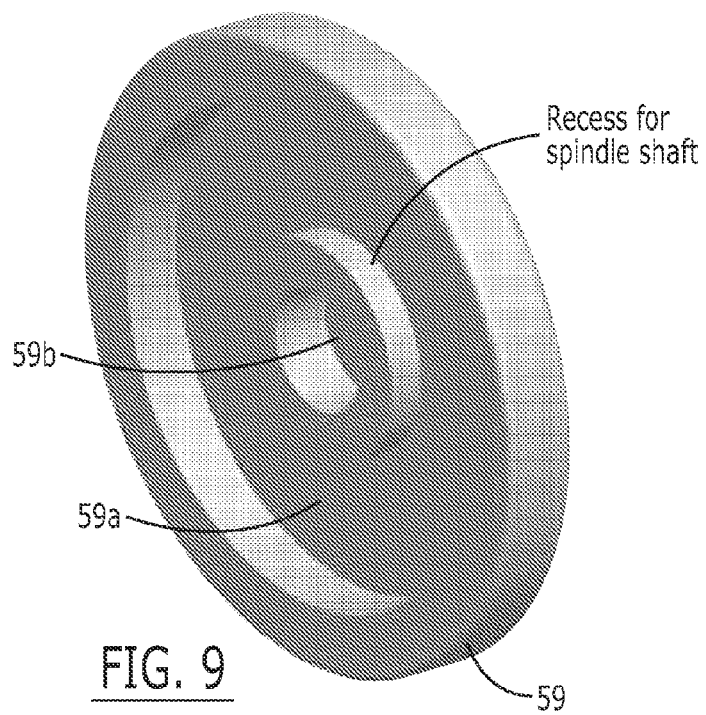
FIG. 9 is a side perspective view of the valve cap.
Figure 10:
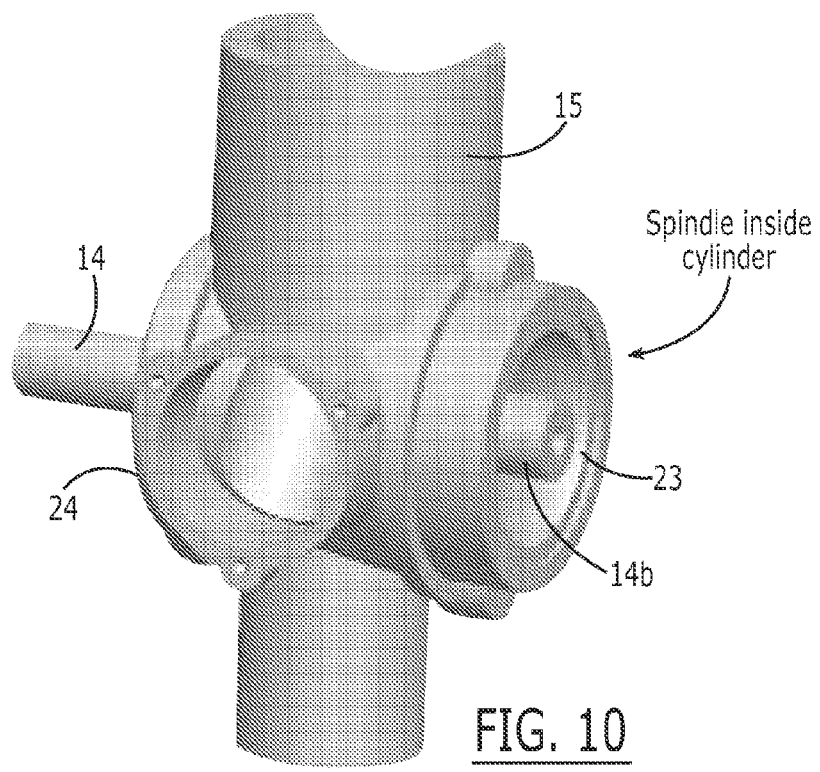
FIG. 10 is a side perspective view of the spindle positioned inside the valve.
Figure 11:
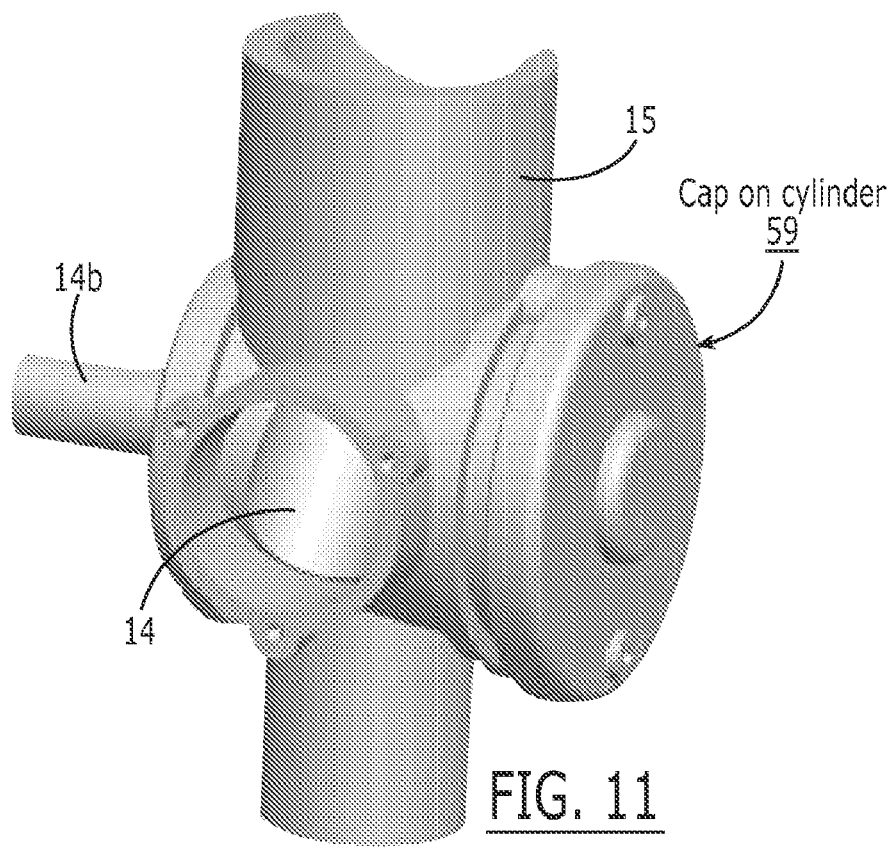
FIG. 11 is a side perspective view of the spindle, valve, and cap assembly.
Figure 12:
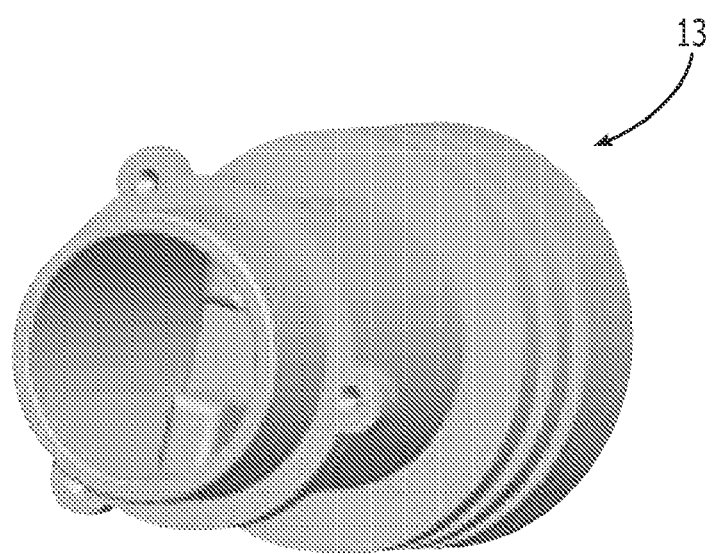
FIG. 12 is a side perspective view of the flow sensor.

Carbon dioxide partial pressure can be measured using non-dispersive infrared (NDIR) spectroscopy technology. It should be noted that the carbon dioxide sensor can be replaced with a real-time oxygen sensor, as real-time oxygen traces morphologically mimic the inverse of carbon dioxide traces. FIG. 8 shows a typical triggering sequence for the valve based on levels of airway flow and exhaled $CO_2$ partial pressure in order to direct the end tidal gas through the condensation chamber of the disposable unit 50.

A second embodiment of the invention involves directing exhalation gas (not end-tidal gas as described above) through the condensation chamber. Such a configuration involves the use of two one-way valves (i.e., check valves) configured in such a way as to let ambient gas flow into the patient on inhalation, and to allow gas to flow through the condensation chamber on exhalation. Such a configuration greatly simplifies the system by eliminating the need for the $CO_2$ and flow sensing systems.

Gas flows through the system starting at the mouthpiece, which is an integral part of the disposable portion 50 of the system 10. Gas flow, as mentioned, may be redirected using a rotary spindle three-way valve assembly or a check valve assembly. The invention is designed to keep exhalation gas residence time within the disposable element 50 high enough to provide acceptable condensate extraction efficiency. In a preferred embodiment, this is accomplished by allowing the breath stream to make multiple passes by the condensation element (described below). In order to avoid patient discomfort, the flow path size and geometry are designed such that exhalation resistance is minimized.

Additionally, exhalation gas dead space, located proximal of the valve system, is minimized, thus reducing patient discomfort during use. This is accomplished by ensuring that the gas pathway proximal to the valve is of minimal volume. All flow pathways are preferably designed to have openings well above 100 mm² to prevent uncomfortable levels of gas flow resistance during use. Only one drop of condensate (approximately 200 microliters), likely produced within five minutes time of patient breathing, and deposited on the concave surface of the miniaturized sensing device, is required for condensate analysis.

In the preferred embodiments, the condensation element 52 comprises a thermally conductive, machinable or moldable material with a distinct inverse pyramidal or icicle-like shape. This shape ensures that condensate collecting on the surface of the element is focused, as it is pulled by gravity, toward the lowermost tip 55. It should be noted that other shapes are possible and that the shape described here is not intended as limiting and is merely one way to ensure optimal condensate accumulation. Further, it should be noted that although FIGS. 1A and 1B show the exhalation gas pathway simply passing by the condensation element in a straight line path, other gas flow configurations are possible, including the use of baffling to direct the exhalation gas in a rotary or cyclonic fashion around the condensation element as a further means of optimizing gas residence time with the goal of increasing spatial condensate accumulation.

The condensation element can be cooled by means of Peltier junction cooling elements in mechanical contact with the element. Other cooling mechanisms are also possible, including radiant cooling, convective cooling, micro-scale or MEMS-based cooling systems, and cooling based on endothermic chemical reaction. The cooling method itself should not be considered to be a limiting element of this invention. Such Peltier junction coolers are shown for concept in FIGS. 1A and 1B but are preferably built into the non-disposable portion 51 of the instrument 10 due to their relatively high cost. Thus the disposable element 50, when plugged into the non-disposable element 51, ensures mechanical contact between this condensation element and the Peltier junction devices. The Peltier junction devices cool the condensation element sufficiently such that vapor and aerosol-phase water in the exhalation gas (typically at BTPS gas conditions) condenses on the element itself, with the rate of condensate accumulation being driven primarily by the gradient in temperature between the surface of the element and the exhaled gas stream and the surface area of contact between the element and the gas stream. With the water, any semi- and non-volatile constituents of the exhaled gas stream, such as volatile organic compounds (VOCs), proteins, or any species trapped in aerosols, accumulate on the condensation element. Any of these constituents may represent target analytes for the miniaturized analysis chip.

The condensate is driven by gravity to accumulate at the lowermost tip 55 of the element. It should be noted that the element may have surface coatings such as wax, Teflon, or other hydrophobic materials to serve the dual purpose of increasing surface tension between the condensate phase and the element, thus promoting smaller surface area between the two, as well as minimizing potential chemical interaction/bonding between the species of interest and the surface of the element. Smaller contact area between the condensate and condensing element decreases drag and increases gravimetrically driven flow of condensate droplets at the condensate tip.

Temperature control of the Peltier junction devices and of the device itself is provided by means of a thermistor-mediated temperature feedback system. In this configuration, a thermistor is preferentially located distant from the Peltier junction devices on the element. An electronic Bang-Bang controller turns on/off current to the Peltier junction devices based on the temperature (resistance value) sensed by the thermistor. Other temperature control schemes such as PID control may be used, and this embodiment is not intended as limiting. In this fashion, Peltier junction devices can be used to generate a known temperature, within some range of error, in the system. The condensation element can be constructed using high-volume manufacturing techniques such as die stamping, cold forging, or injection molding to ensure a low cost of manufacture.

The aforementioned condensate, containing water as the primary matrix along with potential analytes such as VOCs, proteins, or other biological or organic species, drops onto the concave collection chamber 53 of the miniaturized analysis device 54. The device 54, which may be in a chip format, then distributes and processes the condensate liquid internally so as to facilitate immediate, automated assessment of constituent species of interest. In a preferred embodiment of the invention, the analysis device "plugs" into the disposable element 50, thus forming a two-piece disposable unit. This configuration ensures that any of a potential number of analysis devices, containing different types of sensors that are sensitive to any of a number of chemical species, can be loaded into the disposable element 50. The analysis device forms a hermetic and pneumatic seal when plugged into the disposable element 50.

External electrical tangs or contacts on the device allow the non-disposable portion 51 of the invention to electrically communicate with the device. These electrical contacts preferably comprise at least one power/ground pair and at least one contact reserved for chip output. Therefore, the non-disposable portion 51 of the invention is likely to have three or more receptacles for three or more electrical contacts on the chip 54. These receptacles on the non-disposable portion 51 of the invention, into which the miniaturized analysis device 54 plugs, are ideally of sufficient quantity and type (input or output) so as to ensure that multiple types of miniaturized analysis devices, having potentially an array of input/output needs, can be accommodated. Further, it is envisioned that the interface to these receptacles, on the non-disposable device 51 side, is under microprocessor control, thus allowing greater flexibility as to voltage and/or current limits and/or operating envelope of the receptacles. Additionally, the non-disposable portion 51 may provide control signals and receive feedback signals from the device in digital or analog form. In a preferred embodiment of the invention, the non-disposable unit 51 may contain circuitry that functions as a potentiostat for controlling and analyzing an electrochemical cell that is implemented via electrodes on the micro-sized analysis device. In this fashion, electrochemical sensors may be used as the functional sensing method of the device.

Any fluid-handling capability and sensors are contained within the analysis device. Fluid movement in the device can be accomplished in any number of ways, including by capillary action, electrophoresis, electrostatic action, vacuum or positive pressure, or even by mechanical pumping means such as pumps (external or integrated into the device) based on displacement of the surface of the device or displacement of a portion of the fluid flow pathway (such as by peristaltic means). Sensor and transducer elements may take any form and be designed to track any desired physiologically or environmentally relevant variable, for example, pH, protein content, or even DNA content. A single chip may contain multiple sensors and different types of analysis chips may be made, each containing a unique set of processing and sensing mechanisms.

A key feature of the analysis system is that it may handle relatively small volumes of liquid condensate sample, from microliters to even smaller volumes, such that minimal collection time is required on the part of a patient (for example, it is estimated that, in order to obtain approximately 200 microliters of breath condensate, less then 5 minutes collection time would be required). Additionally, like the condensation element, the analysis device is to be constructed using high-volume manufacturing techniques such as die stamping, cold forging, or injection molding to ensure a low cost of manufacture and disposability.

High-volume/low-cost techniques and materials can be used for the manufacture of all elements of the disposable element 50, including the microfluidic device itself. Such techniques may include injection molding of the body of the disposable element, of the spindle, and of the micro-analysis chip. Other manufacturing techniques are also intended to be subsumed within the scope of the invention.

Figure 13B:
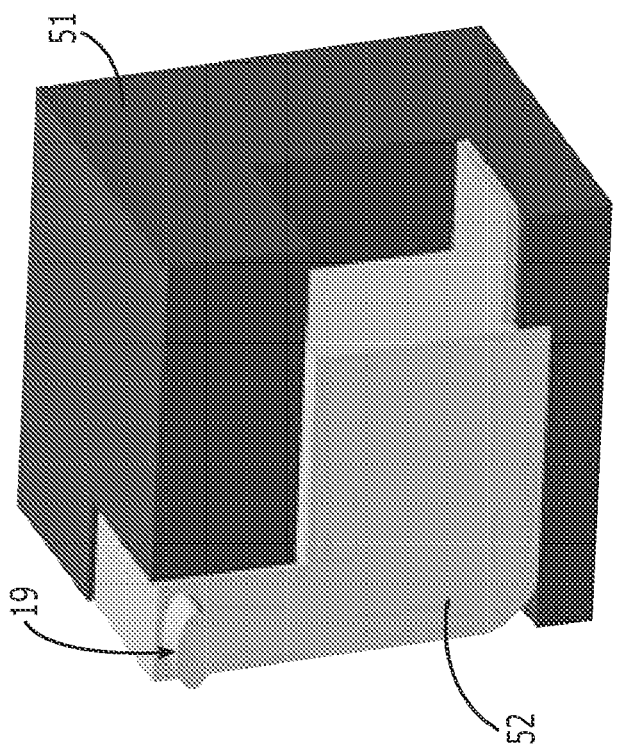
FIGS. 13A and 13B illustrate the mating of the condensate trap with the housing.
Figure 13A:
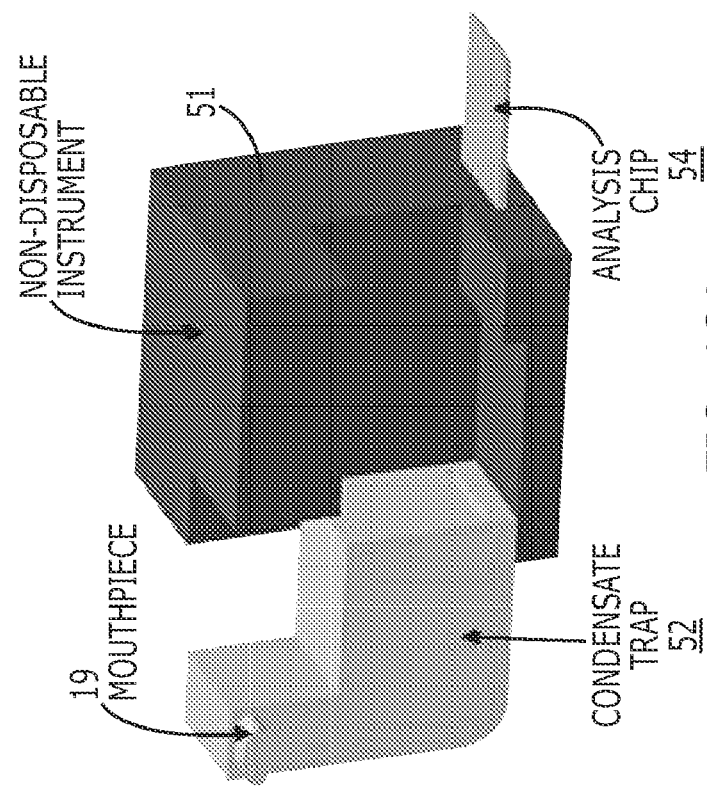

The non-disposable instrument 51 that accompanies the above-described valve, condensation, and analysis systems contains the requisite electronics, and input/output mechanisms for operation of the device. It may provide the source of power for the device, and contain the circuitry, software, and sensors to operate the valve system, the condensation cooling element, and whatever operations are required by the analysis system. It may contain a display for feedback to the user, as well as mechanisms for input by the user. The instrument may also contain capabilities for processing patient information and providing advice for further medical attention. The instrument may attach to the disposable constructs in a simple, easy-to-use manner and minimize contact with the sampling medium (i.e., breath) in order to prevent contamination and minimize cleaning requirements. The instrument may provide any electrical, optical, and fluid connections to the analysis chip and condensate trap required for controlling and monitoring each component. FIGS. 13A and 13B present a simplified representation of how the instrument 10 and disposable constructs may fit together to form the functional device. It should be noted that each component represents only one possible implementation. For the non-disposable instrument 51 and analysis chips 54 in particular, many possible implementations may be possible to form a functional unit with the condensate trap 52.

Another feature of the device, which is conferred at least in part by its modular nature, is that the components that are intended in a particular embodiment to be disposable can be wide-ranging. For example, the chips 54 and disposable element 50 can comprise any of a number of devices known in the art or not yet developed. In order to provide for a plurality of interfaces, the non-disposable device 51 can include an element, typically electronic, for identifying a component when connected, such as a means for reading an identifier from the disposable element 50,54 and then establish communication with the appropriate hardware, software, or other device settings, such as, but not intended to be limited to, temperatures, signal amplification, software, signal location, component voltages, etc.

An identifier could take the form of an ID component, such as, but not intended to be limited to, a variable resistance between components, RFID, MFID, IR and other optical techniques, and IDs stored in memory that can be accessed by the non-disposable unit 51. Electronics could also be adapted to download new software such as component drivers via a local storage device or by accessing the Internet, such as via a wireless signal. The disposable components 50,54 can also comprise a memory chip containing software/data, such as calibration data, necessary for communication with the non-disposable 51, or could even comprise their own digital logic. The IDs/data stored on the disposables 50,54 can also be used for tracking shipments and detecting bad sensors from known bad manufacturing runs, or detecting incompatibilities between software available and sensors, or if the user assembles incompatible parts in the system 10.

Thus it can be seen that the present invention contemplates great flexibility in construction and use, and is not limited by examples given herein.

As one example of how the proposed invention might operate, such a device 10 might be used to measure the pH of a patient's exhaled condensate in order to predict onset of asthma. The patient begins by opening a sealed package containing a small chip-based sensor system 54, specialized for pH measurement, and plugging this chip 54 into the disposable valve/condensation element construct 50 (also obtained from a sealed package). This setup is in turn connected to the handheld, non-disposable electronics instrument 51 by a simple "clip-on" mechanism. The patient then turns on the device 10 and reads directions from a small LCD display and/or speaker located on the instrument 10. Upon powering, the instrument 10 prepares for condensate collection by activating the cooling system and various sensors. Upon a signal from the instrument 10, the patient positions the instrument 10 close to the face, then places his/her mouth on the provided mouthpiece 19 and begins to inhale and exhale normally. The instrument 10 monitors total breath volume and determines the amount of collection time necessary. When such time is complete, the instrument 10 again signals the patient, by display or sound, and the patient removes his/her mouth from the mouthpiece 19 and then sets the instrument 10 down.

The instrument 10 then automatically proceeds with sample analysis of the collected breath condensate. Once the pH level is determined, the information can be reported on the LCD, saved to on-board memory, and/or beamed wirelessly to another system. As an alternative, the instrument 10 can also take other user input, such as age, weight, etc., and perform on-board calculations to estimate and report the patient's risk for asthma. The patient can then be advised to seek further medical attention. When the analysis is completed, the instrument 10 signals for disposal of the valve/condensation element/analysis chip construct 50. The patient detaches this construct 50 from the non-disposable instrument 51 and places it in an appropriate waste receptacle.

In another embodiment of the present invention, believed at the time of filing to represent the best mode thereof, the surface of the condensation element mimics the surface structures and patterning of coatings seen on the wings of a desert beetle that collect water from a foggy atmosphere. These wings exhibit condensation of water vapor without the need for a cooling device and the channeling of condensed water to the mouth. The structure on the beetle's back is composed of interconnected super-hydrophobic troughs and isolated hydrophilic mounds. During morning fog and wind in the beetle's native desert habitat, the beetle tilts its back upward and toward the wind to collect the fog droplets, which are approximately 1-40 μm in diameter. As the droplets strike the surface, they bounce off hydrophobic sections and cling to hydrophilic sections until they build enough mass to overcome capillary forces on the hydrophilic mounds. The droplet then rolls down, following the hydrophobic path.

The features of condensation without external cooling and the ability to channel condensed water are important for breath condensate collection and analysis. Removing the constraint of a cooling system (technically challenging for handheld implementation) for condensation is extremely beneficial in the design of a small handheld EBAC collector. This embodiment achieves condensation without an external cooling system by patterning of surface coatings and structures of various shapes and dimensions. Surface coatings have been evaluated to determine sample contamination and loss.

A particular hydrophobic or super-hydrophobic surface is provided onto which are created relatively hydrophilic areas. Under vapor stream, a super-hydrophobic surface repels water vapor and allows it to collect and accumulate on hydrophilic spots to accumulate into drops. The accumulated water can gain enough mass to overcome the binding forces on hydrophilic spots and roll down hydrophobic channels areas into a collection vessel.

Super-hydrophobic and super-hydrophilic surfaces have been created in the prior art that have an enhanced capability to guide water through microchannels. One procedure uses a polyelectrolyte multilayer (PEM) composed of poly(allylamine hydrochloride) (PAH) and poly(acrylic acid) (PAA), which is decorated with PAH/silica nanoparticles. The entire structure is coated with semi-fluorosilane using chemical vapor deposition (CVD). By immersing the PAH/PAA PEM in an acid bath, a micro-pore network is formed on a micron scale. The nanoparticles provide surface roughness at the nano-scale. These two surface treatments create the multi-length network of pores and bumps necessary for the formation of a super-hydrophobic surface. The contact angle of the surface could be as high as 172°.

In an exemplary embodiment, not intended to be limiting, 2-propanol solution was used to deliver polyelectrolytes (polyflourescein isothiocyanate allylamine hydrochloride) (FITC-PAH) through the semi-fluorosilane layer that would effectively latch on to the underlying PAH/PAA polyelectrole layer, yet stick out beyond the hydrophobic surface to create regions of hydrophilicity. The results showed an advancing contact angle of 144° and a receding contact angle of 12°, which proved sufficient for wetting the hydrophilic FITC-PAH spots, and water could spread out entirely along the length of micron-width hydrophilic channels. In terms of vapor collection, after spraying mist on the surface, it was observed that water did not wet the super-hydrophobic surface, but became perfect spheres, and eventually stuck to the patterned hydrophilic areas to form large droplets. The super-hydrophobic surface also needed only a 2° angle of inclination to initiate rolling of a 4 mg water droplet. These surfaces have been incorporated into a device that can collect enough moisture with a minimum number of breaths and that can help guide water molecules to an e-nose for chemical analysis.

Another technique is photochemical modification using UV light and a reducing agent. A few minutes exposure rapidly changes the contact angle from 80° to an average 50° after only 5 minutes of exposure. The contact angle, however, prior to UV treatment, is too low for the hydrophobic portion (although treating with ion-etching, vacuum deposition, or extensions may help).

To determine the ease with which liquid could be collected at the tip of a condensation element, different types of surface coatings were explored. Coatings that were hydrophilic, hydrophobic, and a combination of the two were evaluated. The combination coatings were created by either spraying or wiping a hydrophilic layer on top of a hydrophobic layer, which created alternating hydrophobic/hydrophilic patterns on the condensing surface. The coatings with a hydrophilic/hydrophobic combination were found to yield the highest mass of condensate, which reinforces the water capture ability of the Namib Desert beetle concept, in that the condensation element requires both hydrophilic and hydrophobic layers to optimally condense the liquid onto the condensation element and pool at a collection well.

Patterning is important in the process of creating hydrophilic areas on super-hydrophobic surfaces. A collection mechanism should preferably comprise a surface that can gather enough vapor to produce a condensate droplet size (similar to the Namib beetle) with enough mass to roll freely down to a reservoir. Inkjet printing can allow for consistent printing of small features, including hydrophilic micro-spots or micro-channels that can help direct droplet rolling to single point to maximize condensate collection.

Figure 14:
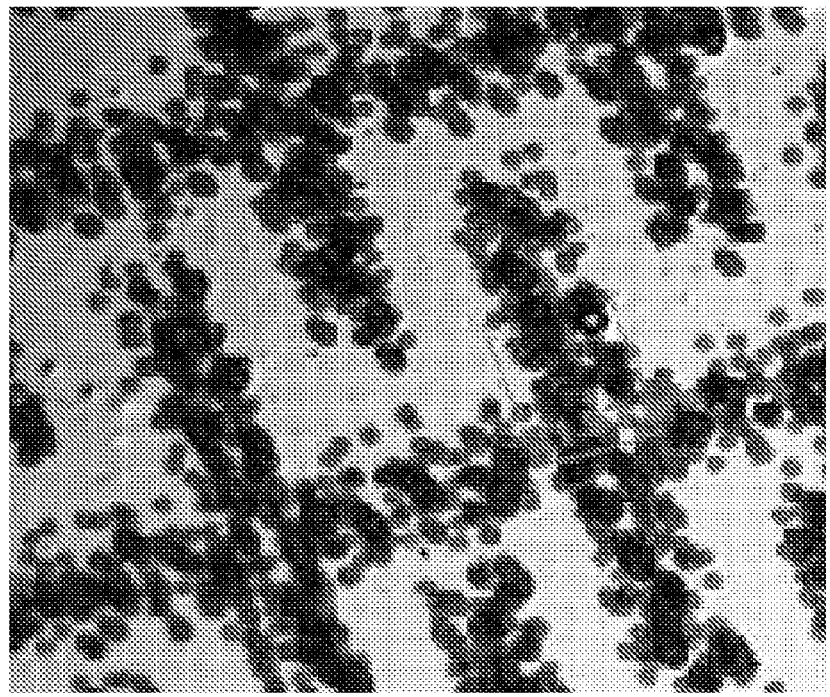
FIG. 14 illustrates an exemplary pattern printed on a Mylar substrate.

Inkjet patterning has been demonstrated in the sub-100-µm scale. Sinter silver colloid conductors can be printed using a modified Epson R220 printer and Mylar substrate (FIG. 14). Silver solutions were custom created in the laboratory and fed into a standard inkjet printing cartridge. Particle size was an important issue, since it was found that printing larger particles (greater than 50 nm) often clogged the 12.4-µm inkjet nozzle. Particles in the 40-nm range (20% w/w in 50:50 water/diethylene glycol) never clogged the print head. Several other practical problems were addressed and resolved in these efforts. Because the compounds of interest are in very low concentration in this study (0.1-1.0% solutions or entirely chemical mixtures), inkjetting the patterns is a viable technique.

Figure 15:
FIG. 15 illustrates a pattern printed on cylindrical shells.
Figure 16:
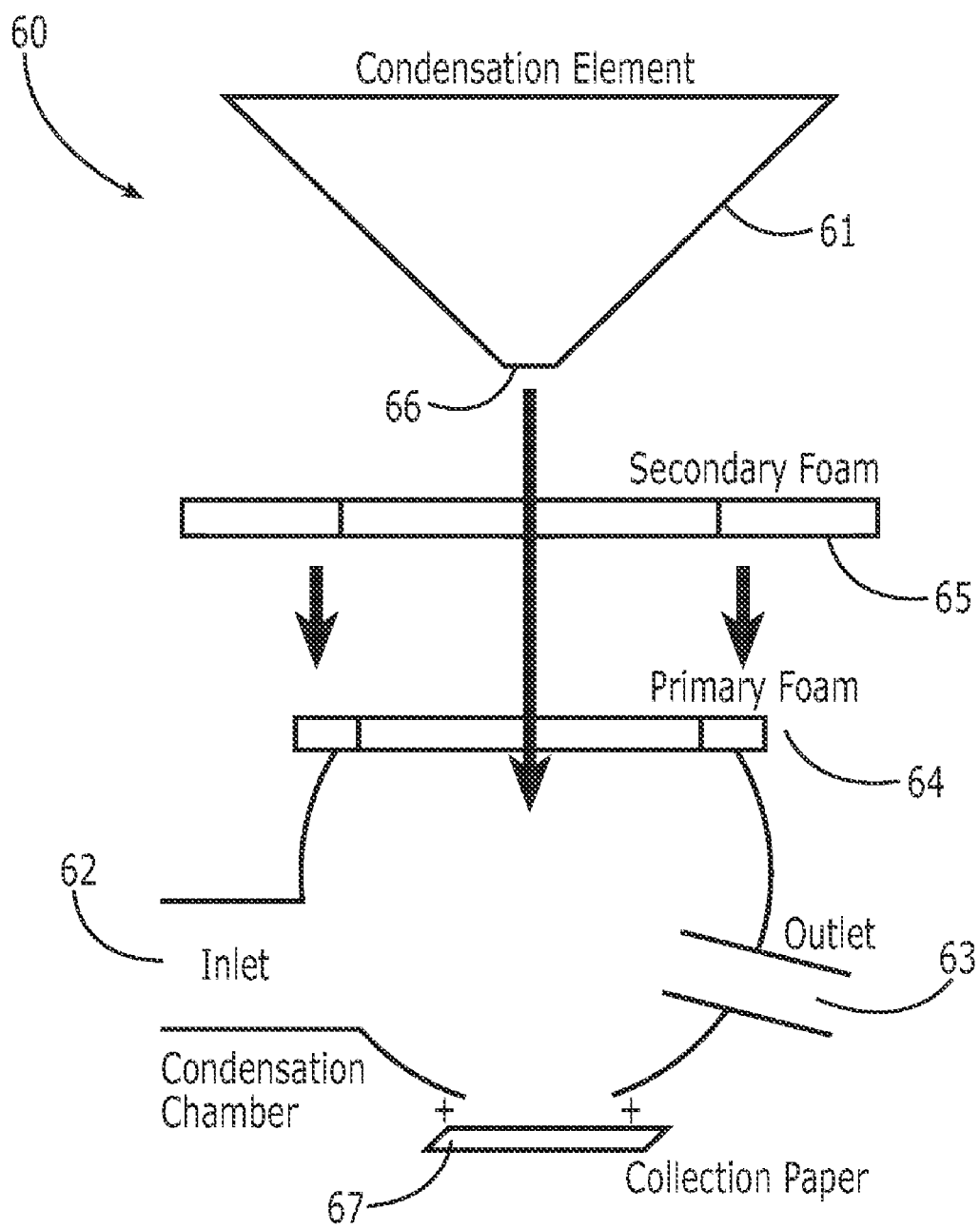
FIG. 16 is a schematic illustration of a condensation chamber.

Three-dimensional surfaces can also be printed on. For example, cylindrical shells can be printed on by modifying the paper feeding mechanism of a Hewlett-Packard DeskJet printer (model #3915). The rubber roller in the paper feed system was removed and replaced with a holding mechanism designed to hold the shell in place while the roller bar rotated the shell and prevented the shell from sliding in a horizontal direction (which causes blurring). Traces were printed using black ink on standard 00 sized capsules. FIG. 15 shows samples of various patterned gelatin capsules. It can be estimated that resolutions in the order of 100 to 200 µm are easily attainable.

An experimental setup was used to investigate how the contact angle that a solid surface forms with water affects the condensation of humidified air. A condensation chamber 60 (FIG. 16) was created with a condensation element 61, inlet 62 and outlet 63 ports for gas flow, and configurable baffling structures to manipulate the flow of gas through the chamber 60. Foam strips 64,65 were used to seal the condensation chamber 60 and element 61 to prevent gas leakage and reduce variability in chamber temperature. The condensation element 61 comprised a cone structure to facilitate the collection of condensate at the tip 66 of the element 61 by gravity. The condensation element 61 was cooled down to 2° C. using ice water and maintained within ±1° C. by regulating the ice water in the element 61. Subjacent to the condensation element 61 was positioned a collection paper 67 for soaking up condensed liquid. The volume of the condensed liquid was calculated by weighing the collection paper 67 before and after it is soaked. A ventilator humidifier (ConchaTherm III Plus) was used to generate humidified gas at 75% humidity and 37° C. The humidified gas was fed into the input port of the condensation chamber at a constant flow rate of 3 L/min. The condensation chamber 60 was exposed to the humidified gas for 20 min to ensure adequate liquid was formed on the condensation element.

Figure 17:
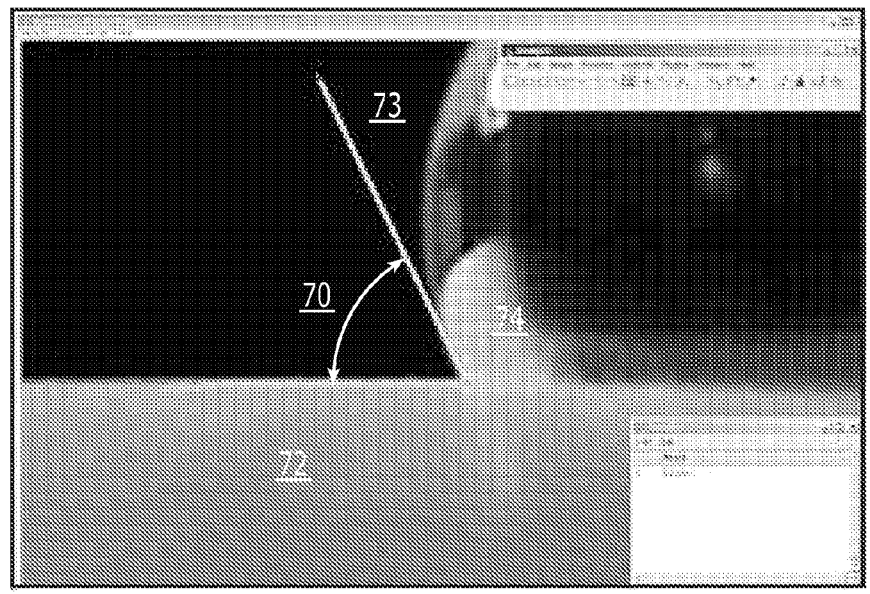
FIG. 17 illustrates the measurement of contact angle.
Figure 18:
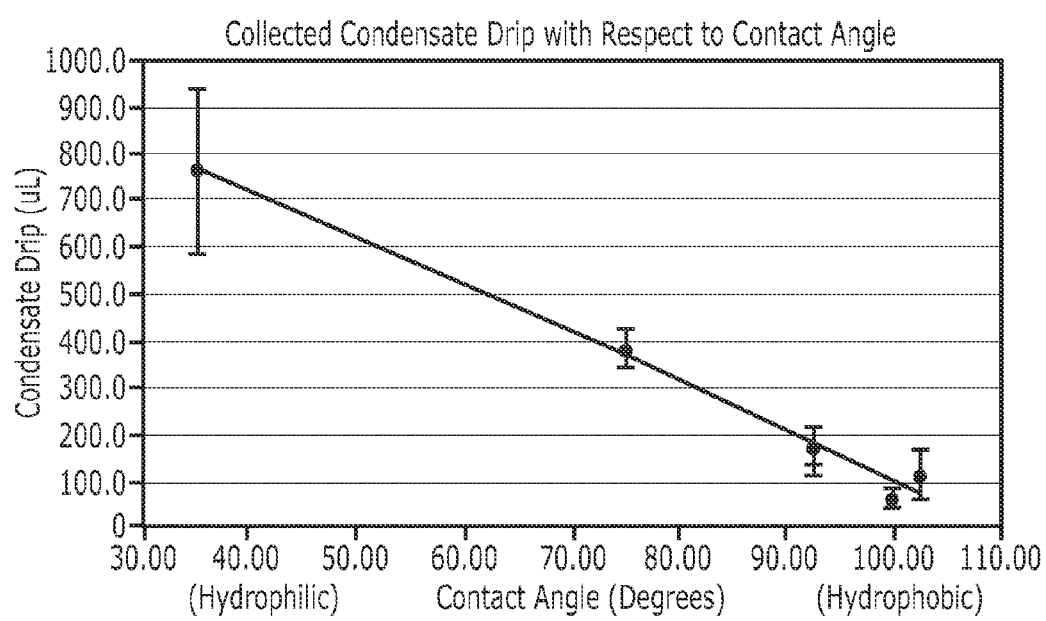
FIG. 18 is a graph of the volume of condensate collected versus contact angle.

Contact angle 70 was measured using the goniometry technique. Contact angle 70 provides a measure of the angle at which a liquid interfaces with a solid surface. An angle less than 90° means the surface is hydrophilic and greater than 90° indicates a hydrophobic surface. Water drops of constant volume were deposited on the surface of the solid substrates, and a high-resolution camera with a macro lens was used for image capture. Imaging software, ImageJ (a public domain image processing software developed at the National Institutes of Health) was used to compute the contact angles 70 from the captured image by measuring the angle formed between the solid 72 and the tangent 73 to the drop surface 74 (FIG. 17). The contact angle 70 was varied from 35° to 100° by using polished stainless steel as the base substrate and then coating this surface with hydrophobic (polyolefin wax) and hydrophilic (Rainex®) materials. It was observed that as the contact angle 70 decreased, the volume of condensate collected on the condensation element 61 increased (FIG. 18), indicating that the more hydrophilic (q<90°) the surface, the higher the efficiency of the condensation element in wicking water away from humidified gas.

Another aspect of the efficiency at which condensation takes place on the condensation element is the dependence on the collision characteristics of the humidified gas with the condensation element. Parameters such as duration of gas exposure to condensation element, the pathway of gas flow against and around the condensation element, and location of the input port have been investigated. The residence time was defined as the duration of gas exposure to the condensation element. This parameter was adjusted by increasing the internal volume of the condensation chamber while maintaining other factors such as inlet port location, flow pathway, surface type, flow rate, and gas volume constant. A 48% increase in residence time produced a 12% increase in the collected condensate volume.

Gas flow pathway inside the chamber was altered using configurable baffling structures to create spherical, conical/helical, and square chambers. All other factors (inlet port location, surface type, flow rate, gas volume etc) were fixed, although it was difficult to maintain a fixed residence time across the chamber designs. Variation in residence time was 3% between the three chambers and considered negligible in terms of its effect on the condensation output. It was observed that a spherical chamber performed the best with an average of 60% more condensate volume than the conical and square chambers. It was hypothesized that this performance increase was due to the small surface-to-volume ratio characteristic to the spherical chamber. There was no significant difference in performance between the conical and square chambers.

The location of the inlet port in the condensation chamber was also adjusted so as to determine whether it was better for the gas to flow from the top of the condensation element to the tip or vice versa. It was observed that having the inlet port at the top of the condensation element increased the collected condensate volume by 30%. Thus it is believed that important considerations in designing a condensation chamber are: controlling the gas flow path inside the chamber using a spherical-type structure, and positioning the inlet port at the top the condensation element so that gas flows toward the tip of the condensation element (in line with the direction of the drop to the collection well).

It has been found, as discussed above, that almost 50% of exhaled breath is dead space gas, gas that does not reach the alveoli and therefore does not participate in lung gas exchange. Alveolar gas is deepest in the lung and is exhaled after the dead space gas that resides in the trachea and larger non-exchanging channels in the lung. For breath analysis to replace blood testing, it is important to sample the alveolar gas only since this is the gas that exchanges compounds with the blood. Furthermore, dead space varies from individual to individual and causes significant variability in measured results if the entire breath is analyzed. One approach to standardize the collection procedure is to utilize the partial pressure of $CO_2$ (since it is a major contributor of exhaled breath) as an indicator of the gas exchange taking place in the lungs.

An integrated end-tidal breath sampling system 75 is provided in the present invention that can interface with existing breath condensate collection devices. The system 75 can comprise a three-way breath valve 49 such as that described above, and a respiratory monitor 36 to divert only end-tidal gas for condensation. The breath valve 49 offers a means to direct the flow of gas with minimal resistance to the subject while breathing. The respiratory monitor 36 is used to determine start of end-tidal gas. Among a variety of parameters, the integrated system 75 computes the end-tidal volume and $CO_2$ of each breath condensed so that it is feasible to standardize the results.

The EBAC collection system 75 of the present invention is based on a passive water extraction process that relies on concepts proven to work in nature, and does not require cooling of the condensation element. The Namib desert beetle has demonstrated a means to extract water from a foggy atmosphere by utilizing its hydrophilic/hydrophobic layered wings. It has also been shown that hydrophilic/hydrophobic surfaces can be synthesized and have been shown to guide water droplets through micro-channels. EBAC can also be extracted on a hydrophilic/hydrophobic surface. Owing to the nature of the hydrophilic/hydrophobic surfaces, the proposed system can eliminate the need for an external cooling system required for condensation. Similar to the Namib desert beetle and the lotus leaf, a condensation element can be made from a substrate coated with hydrophilic spots to attract water from the breath as it comes in contact with the condensation element. The substrate is also coated with super-hydrophobic channels that converge together. The channels help direct the condensed droplets to the collection well. Further, since cooling is not used in this embodiment, the system 75 may preferentially collect breath aerosol over breath condensate, which may provide a higher concentration of analytes found in aerosol form.

Figure 19:
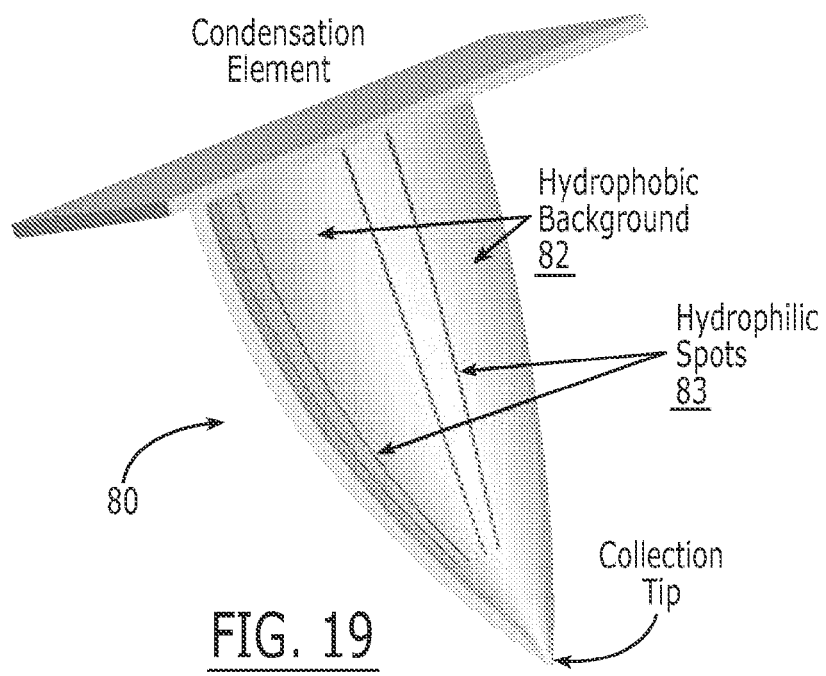
FIG. 19 is a side perspective view of an exemplary condensation element.
Figure 20:
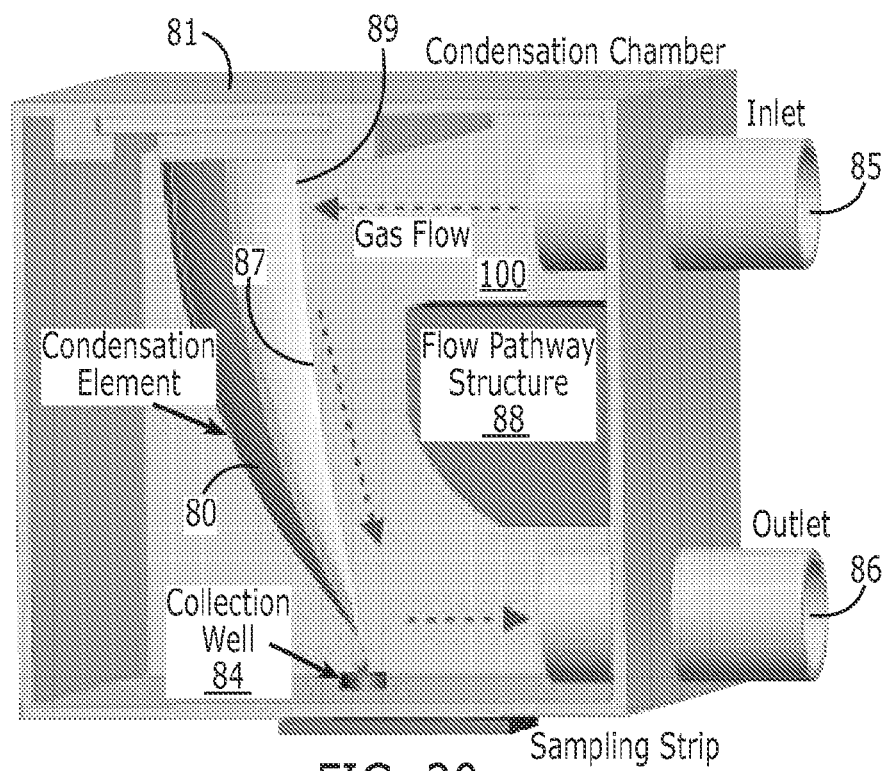
FIG. 20 is a side perspective view of an exemplary EBAC collection device, incorporating the condensation element of FIG. 19.

One possible shape of the condensation element 80 is that of an inverted triangle, a substantially conical shape (FIG. 19). The element 80 is oriented substantially vertically in the interior space 100 of a condensation chamber 81 to take advantage of gravity, along with the super-hydrophobic channels 82 aligned with hydrophilic regions 83, to incite condensed droplets to roll down the element 80 and into the collection well 84 (FIG. 20). The condensation chamber 81 directs the exhaled breath onto the condensation element 80. In a preferred embodiment, the inlet port 85 of the condensation chamber 81 is positioned substantially vertically aligned with and above the outlet port 86, and pointing substantially at the top 89 of the condensation element 80. Further, the condensation element's conical shape has a bend 87 in a direction substantially facing the inlet 85 and outlet 86 ports.

A baffle element 88 can be positioned within and extend into the condensation chamber's interior space 100 at a height between the inlet port 85 and the outlet port 86. The baffle element 88 can serve to form a fluid pathway (shown in dotted lined in FIG. 20) from the inlet port 85 to the condensation element's top, downward and between the condensation element 80 and the baffle element 88, and out the outlet port 86.

Figure 21:
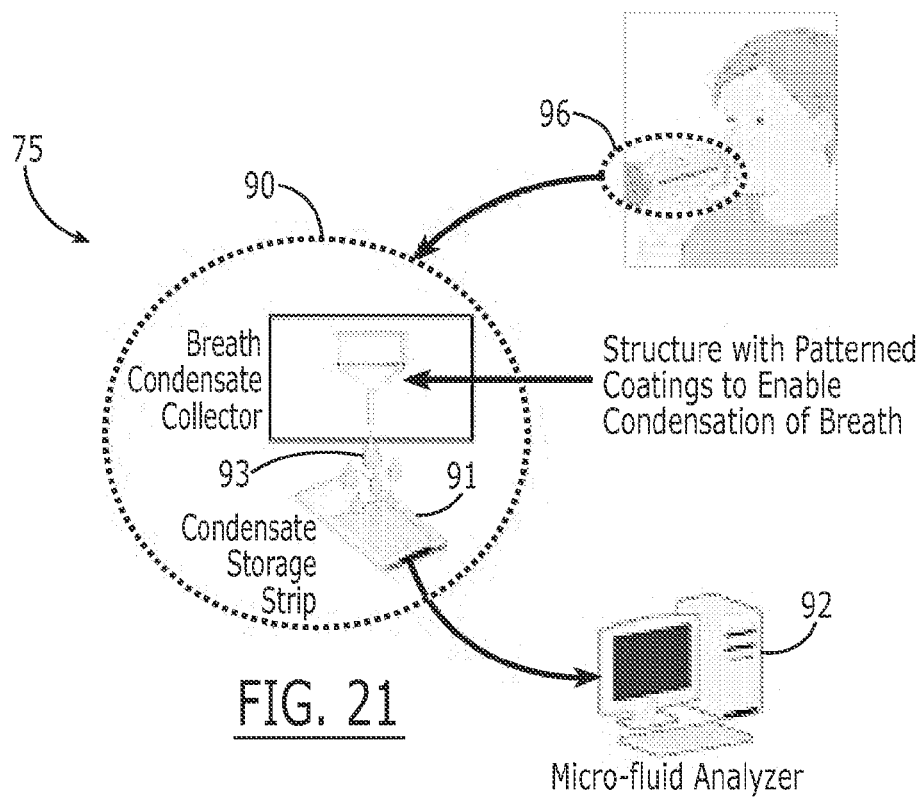
FIG. 21 illustrates the use of the passive exhaled breath collection system.
Figure 22:
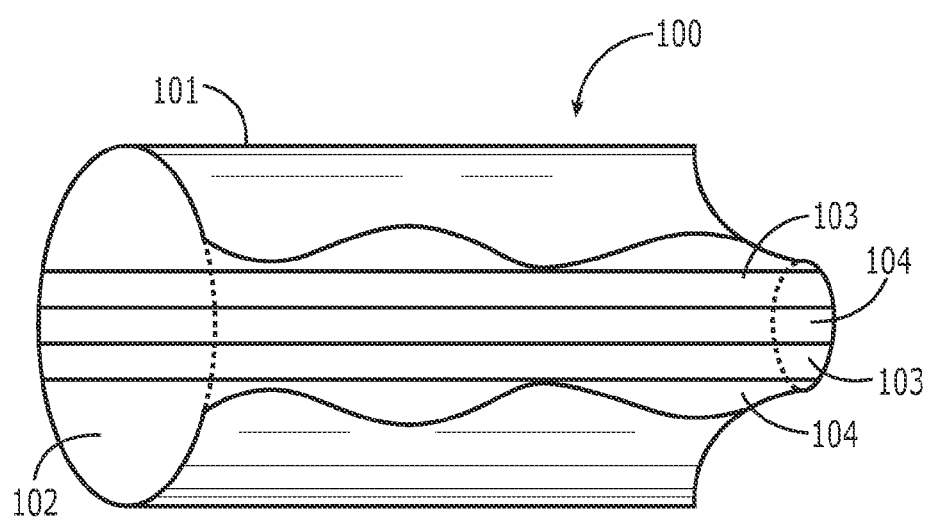
FIG. 22 is a schematic illustration of a cylindrical collection chamber, partially cut away along the longitudinal axis to display the interior surface.

With the advent of microfluid analyzers and micro-chemical sensors, the need for large sample volumes for analysis has been lifted. Current EBC collectors cannot be directly interfaced to such micro analyzers. The present system 75 comprises an EBAC collector 90 with an interface that accommodates a sampling cartridge 91 that can be injected into a desktop analyzer 92 (FIG. 21). The condensate 93 pools directly into the sampling cartridge 91 and eliminates the need to manually pipette it from the collection vessel. In an alternate embodiment, a completely integrated system comprises an EBAC collector that is directly interfaced with a micro-chemical chip so that collection and analysis are performed in situ with complete portability.

The efficacy of a hydrophobic/hydrophilic surface can improve the performance of other types of condensation chambers as well. In a simple example, not intended to be limiting, the condensation chamber 100 (FIG. 22) can comprise a cylindrical element 101 having in interior surface 102 at least a portion of which is coated with alternating hydrophobic 103 and hydrophilic 104 regions. This arrangement can minimize or eliminate entirely the need for cooling the chamber 100 while still enhancing the condensation-collecting ability to yield sufficient condensate for analysis.

The small sample volume required in the present invention also means that sampling time can be reduced. A study of contact angle and surface coatings yielded collection volumes of 500 µL for 5 min of exposure to humidified gas. Since many known chemical analyzers only require 100-200 µL of sample volume, this target volume can be achieved in less than 5 min.

Since it has been shown that the condensation of breath markers is influenced by the condensation temperature, markers that are invariant to condensation temperature can be selected. For instance, similar concentrations of hydrogen peroxide ($H_2O_2$) and malondialdehyde (MAD) were observed when EBAC was condensed at −10° C. and 5° C., albeit, as expected, smaller condensate volume was observed at higher condensation temperatures. In addition, for other markers, such as ammonia, it is better to collect at a higher temperature than 0° C. because of readings of higher concentration at elevated temperatures. These markers have been associated with various disease states and are therefore of interest.

The present invention has numerous advantages, among which is the elimination of external cooling system, thereby reducing weight and manufacturing cost. By far the largest and most complex components of current breath condensation devices are for chilling the breath. Removing these refrigeration components is a breakthrough in creating low-cost, small breath collection systems.

Another advantage is the collection of EBAC into a standardized sampling cartridge that can be directly interfaced with existing microfluid analyzers, thereby minimizing the number of steps to transfer the condensate to an analytical station. The need for fewer intermediate steps helps minimize the sample processing time and risk of contamination due to mishandling of samples.

A further advantage is that a short collection time also allows for higher sampling frequency, meaning fewer samples averaging over time, which provides a more accurate representation of an instantaneous physiological state, helping to reduce variability between samples.

Liquid chemical sensors can be interfaced with the EBAC collection unit of the present invention, such that the condensate drips directly onto the sensing chip. This arrangement creates an integrated handheld system that extracts, collects, and analyzes EBAC. Such a device is applicable in clinical settings, among others.

The present invention is ideal for use with microfluidics, since microfluid analyzers can be interfaced with the EBAC collector and even further reduce sample volumes needed for analysis, thereby decreasing the collection time even further.

The above examples highlight a benefit of the embodiments of the current invention. A micro-scale sample collection and delivery system obviates the need for large sample sizes (i.e., 1-5 milliliters) and allows for only 200 microliters or less to be used. This in turn allows for short collection time (under 5 min) and thus eases patient discomfort and reduces risk for error committed by the patient. The device is disposable, which makes multiple collections simple and inexpensive, and obviates worries over instrument cleaning and maintenance. Finally, the above example demonstrates the benefit of real-time results. Results can be presented at point-of-care and without the intervention of a trained technician.

Another important benefit not highlighted in the example is the flexibility of the overall design, which allows for many types of analytical applications to be accomplished. Using the same condensate trap design, microfluidic interfaces, and electrical interfaces, many types of sensors and transducing methods can be incorporated into the device in a "plug-and-play" fashion. From the user point-of-view, such modifications are invisible, and operation of the device remains simple and constant. However, depending on the type of analytical chip and non-disposable instrument used, a large variety of analytes may be tested for, and an essentially unlimited number of advanced signal processing methods may be employed to guide further medical action.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A system for collecting an exhaled breath sample from a subject comprising:
   a condensation chamber having an outer wall defining an interior space, the outer wall having an inlet port and an outlet port therethrough in fluid communication with the interior space, the inlet port placeable in fluid communication with an exhaled breath sample of the subject;
   a condensation element positioned within the condensation chamber interior space, the condensation element having a shape tapering downwardly toward a bottom tip thereof;
   means for enhancing a condensation of fluid on the condensation element; and
   a collection area positioned within the condensation chamber interior space beneath the condensation element bottom tip, for collecting condensate accumulating on an outer surface of the condensation element and dropping from the tip thereof.

2. The system recited in claim 1, wherein the condensation-enhancing means comprises a means for cooling the condensation element below ambient temperature.

3. The system recited in claim 2, wherein the condensation element has a space therein in thermal communication with the outer surface, the space adapted for holding a cooling fluid.

4. The system recited in claim 2, wherein the condensation-enhancing means comprises an electronic cooling means in thermal contact with the condensation element.

5. The system recited in claim 1, wherein the condensation-enhancing means comprises the condensation element outer surface, the outer surface comprising alternating hydrophobic and hydrophilic regions, the hydrophilic regions shaped to channel condensate in a substantially vertical direction toward the tip.

6. The system recited in claim 1, wherein the condensation element has a substantially conical shape.

7. The system recited in claim 6, wherein the condensation element conical shape has a bend in a direction substantially facing the inlet port.

8. The system recited in claim 6, further comprising a baffle element positioned within and extending into the condensation chamber interior space at a height between the inlet port and the outlet port, for forming a fluid pathway from the inlet port to the condensation element top, downward and between the condensation element and the baffle element, and out the outlet port.

9. The system recited in claim 1, wherein the inlet port of the condensation chamber is positioned above the outlet port to maximize residence time of the sample in the chamber.

10. The system recited in claim 9, wherein the inlet port of the condensation chamber is positioned to direct fluid toward a top of the condensation element, and the outlet port is positioned adjacent a bottom of the condensation chamber.

11. The system recited in claim 1, further comprising a sample collection element removably positionable in fluid communication with the collection area, for receiving condensate therefrom, and for storing the received condensate for subsequent analysis.

12. The system recited in claim 1, further comprising a sample collection element removably positionable in fluid communication with the collection area, for receiving condensate therefrom, and wherein the sample collection element comprises means for analyzing the condensate in situ.

13. The system recited in claim 1, wherein the condensation chamber is substantially spherical.

14. A method for collecting an exhaled breath sample from a subject comprising the steps of:
   placing an inlet port of a condensation chamber in fluid communication with an exhaled breath sample of the subject, the condensation chamber having positioned therein a condensation element, the condensation element having a shape tapering downwardly toward a bottom tip thereof;
   enhancing a condensation of fluid on the condensation element; and
   collecting condensate accumulating on an outer surface of the condensation element and dropping from the tip thereof.

15. The method recited in claim 14, wherein the condensation-enhancing step comprises cooling the condensation element below ambient temperature.

16. The method recited in claim 15, wherein the condensation-enhancing step comprises placing a cooling fluid in thermal communication with the outer surface of the condensation element.

17. The method recited in claim 15, wherein the condensation-enhancing step comprises using an electronic cooling means that has been placed in thermal contact with the condensation element.

18. The method recited in claim 14, wherein the condensation-enhancing step comprises providing the condensation element outer surface that comprises alternating hydrophobic and hydrophilic regions, the hydrophilic regions shaped to channel condensate in a substantially vertical direction toward the tip.

19. The method recited in claim 14, wherein the condensation element has a substantially conical shape.

20. The method recited in claim 19, wherein the condensation element conical shape has a bend in a direction substantially facing the inlet port.

21. The method recited in claim 14, wherein the inlet port of the condensation chamber is positioned substantially vertically aligned with and above the outlet port.

22. The method recited in claim 21, wherein the condensation-enhancing step comprises directing incoming fluid toward a top of the condensation element, and wherein the outlet port is positioned adjacent a bottom of the condensation chamber.

23. The method recited in claim 22, wherein the condensation-enhancing step comprises forming a fluid pathway from the inlet port to the condensation element top, downward and between the condensation element and a baffle element, and out the outlet port, the baffle element positioned within and extending into the condensation chamber at a height between the inlet port and the outlet port.

24. The method recited in claim 14, further comprising the steps of receiving condensate using a sample collection element and storing the received condensate for subsequent analysis.

25. The method recited in claim 14, further comprising the steps of receiving condensate using a sample collection element and analyzing the condensate in situ using an analytical device incorporated with the sample collection element.

26. The method recited in claim 14, wherein the condensation-enhancing step comprises providing a condensation chamber that is substantially spherical.

27. A portable instrument for quickly collecting and analyzing a microfluid sample of breath condensate from a subject, the instrument comprising:
   a portable breath collection chamber having an inlet port and an outlet port, the inlet port dimensioned to pass exhaled breath from the subject into the collection chamber;
   means within the collection chamber for enhancing condensation of a microfluid sample of exhaled breath of the subject; and
   means with the portable collection chamber for analyzing the condensed microfluid sample.

28. The portable instrument recited in claim 27 wherein the enhancing means comprises a condensation element capable of collecting an analyzable microfluid sample on the order of 200 microliters or less.

29. The portable instrument recited in claim 27 wherein the condensation enhancing means comprises a disposable element.

30. The portable instrument recited in claim 27 wherein the enhancing and analyzing means are capable of collecting and analyzing the microfluid sample within about five minutes or less.

* * * * *